United States Patent
Lynch et al.

(10) Patent No.: US 12,138,333 B2
(45) Date of Patent: *Nov. 12, 2024

(54) RHEOLOGICAL SOLID COMPOSITION FOR USE IN PERSONAL CARE COMPOSITIONS

(71) Applicant: The Procter & Gamble Company, Cincinnati, OH (US)

(72) Inventors: Matthew Lawrence Lynch, Mariemont, OH (US); Brandon Philip Illie, Felicity, OH (US); Taotao Zhu, West Chester, OH (US); Philip Andrew Sawin, Wyoming, OH (US); Jamie Lynn Dria, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 55 days.

This patent is subject to a terminal disclaimer.

(21) Appl. No.: 17/225,148

(22) Filed: Apr. 8, 2021

(65) Prior Publication Data

US 2021/0330565 A1 Oct. 28, 2021

Related U.S. Application Data

(60) Provisional application No. 63/007,967, filed on Apr. 10, 2020.

(51) Int. Cl.
| | |
|---|---|
| *A61K 8/36* | (2006.01) |
| *A61K 8/02* | (2006.01) |
| *A61K 8/04* | (2006.01) |
| *A61K 8/20* | (2006.01) |
| *A61K 8/34* | (2006.01) |
| *A61K 8/42* | (2006.01) |
| *A61K 8/73* | (2006.01) |

(Continued)

(52) U.S. Cl.
CPC ............ *A61K 8/361* (2013.01); *A61K 8/0245* (2013.01); *A61K 8/044* (2013.01); *A61K 8/20* (2013.01); *A61K 8/347* (2013.01); *A61K 8/42* (2013.01); *A61K 8/73* (2013.01); *A61Q 15/00* (2013.01); *A61K 2800/48* (2013.01); *A61Q 19/10* (2013.01)

(58) Field of Classification Search
None
See application file for complete search history.

(56) References Cited

U.S. PATENT DOCUMENTS

| | | |
|---|---|---|
| 823,725 A | 6/1906 | Hayden |
| 3,293,684 A | 12/1966 | Otto |
| 3,956,158 A | 5/1976 | Donaldson |

(Continued)

FOREIGN PATENT DOCUMENTS

| | | |
|---|---|---|
| CA | 680113 A | 2/1964 |
| CN | 107440935 A | 12/2017 |

(Continued)

OTHER PUBLICATIONS

All Office Actions; U.S. Appl. No. 17/485,906, filed Sep. 27, 2021.

(Continued)

*Primary Examiner* — Kyung S Chang
(74) *Attorney, Agent, or Firm* — Kathleen Y. Carter; James E. Oehlenschlager

(57) ABSTRACT

A rheological solid composition comprising a crystallizing agent and an aqueous phase.

7 Claims, 3 Drawing Sheets

(51) Int. Cl.
*A61Q 15/00* (2006.01)
*A61Q 19/10* (2006.01)

(56) References Cited

U.S. PATENT DOCUMENTS

| | | | |
|---|---|---|---|
| 4,107,289 A | 8/1978 | Kaufman |
| 4,203,857 A | 5/1980 | Dugan |
| 4,322,400 A | 3/1982 | Yuhas |
| 4,486,404 A | 12/1984 | Weinert |
| 4,806,340 A | 2/1989 | Gaffar |
| 4,808,467 A | 2/1989 | Suskind et al. |
| 5,144,729 A | 9/1992 | Austin et al. |
| 5,160,739 A | 11/1992 | Kanga |
| 5,340,492 A | 8/1994 | Kacher et al. |
| 5,340,571 A | 8/1994 | Grace |
| 5,425,892 A | 6/1995 | Taneri et al. |
| 5,436,278 A | 7/1995 | Imashiro et al. |
| 5,525,397 A | 6/1996 | Shizuno et al. |
| 5,585,092 A | 12/1996 | Trandai et al. |
| 5,605,681 A | 2/1997 | Trandai et al. |
| 5,691,035 A | 11/1997 | Chappell et al. |
| 5,846,520 A | 12/1998 | Guskey et al. |
| 5,916,590 A | 6/1999 | Cody et al. |
| 6,042,815 A | 3/2000 | Kellner et al. |
| 6,143,393 A | 11/2000 | Abe et al. |
| 6,241,835 B1 | 6/2001 | Abe et al. |
| 6,245,413 B1 | 6/2001 | Kenmochi et al. |
| 6,329,308 B1 | 12/2001 | Kenmochi et al. |
| 6,550,092 B1 | 4/2003 | Brown et al. |
| 6,554,937 B1 | 4/2003 | Kenmochi et al. |
| 6,774,070 B1 | 8/2004 | Kenmochi et al. |
| 6,777,064 B1 | 8/2004 | Brown et al. |
| 6,797,357 B2 | 9/2004 | Fereshtehkhou et al. |
| 6,813,801 B2 | 11/2004 | Tanaka et al. |
| 6,936,330 B2 | 8/2005 | Fereshtehkhou et al. |
| 7,003,856 B2 | 2/2006 | Hayashi et al. |
| 7,041,277 B2 | 5/2006 | Holme |
| 7,291,359 B2 | 11/2007 | Haskett et al. |
| 7,386,907 B2 | 6/2008 | Otsuka et al. |
| 7,560,398 B2 | 7/2009 | Zillig et al. |
| 7,566,671 B2 | 7/2009 | Hoadley et al. |
| 7,712,178 B2 | 5/2010 | Yamada |
| 7,779,502 B2 | 8/2010 | Fujiwara et al. |
| 7,937,797 B2 | 5/2011 | Tsuchiya et al. |
| 8,075,977 B2 | 12/2011 | Curro et al. |
| 8,093,192 B2 | 1/2012 | Liu et al. |
| 8,146,197 B2 | 4/2012 | Yamada |
| 8,151,402 B2 | 4/2012 | Takabayashi et al. |
| 8,161,594 B2 | 4/2012 | Policicchio et al. |
| 8,186,001 B2 | 5/2012 | Tsuchiya et al. |
| 8,225,453 B2 | 7/2012 | Yamada |
| 8,245,349 B2 | 8/2012 | Tsuchiya et al. |
| 8,435,625 B2 | 5/2013 | Ruehe et al. |
| 8,528,151 B2 | 9/2013 | Przepasniak |
| 8,536,074 B2 | 9/2013 | Fereshtehkhou et al. |
| 8,617,685 B2 | 12/2013 | Yamada |
| 8,646,144 B2 | 2/2014 | Wada et al. |
| 8,752,232 B2 | 6/2014 | Otsuka et al. |
| 8,756,746 B2 | 6/2014 | Policicchio |
| 8,763,197 B2 | 7/2014 | Policicchio et al. |
| 8,793,832 B2 | 8/2014 | Yamada |
| 8,851,776 B2 | 10/2014 | Schwarz et al. |
| 8,858,971 B2 | 10/2014 | Rao |
| 9,113,768 B2 | 8/2015 | Wada et al. |
| 9,198,553 B2 | 12/2015 | Policicchio |
| 9,204,775 B2 | 12/2015 | Pung et al. |
| 9,296,176 B2 | 3/2016 | Escaffre et al. |
| 9,339,165 B2 | 5/2016 | Vetter et al. |
| 9,622,943 B2 | 4/2017 | Scala et al. |
| 10,076,583 B2 | 9/2018 | Lynch |
| 10,143,764 B2 | 12/2018 | Lynch |
| 10,821,056 B2 | 11/2020 | Swartz et al. |
| 10,835,455 B2 | 11/2020 | Payne et al. |
| 10,932,996 B2 | 3/2021 | Baig et al. |
| 11,812,909 B2 | 11/2023 | Lynch |
| 2001/0048933 A1 | 12/2001 | L. Alloret |
| 2002/0160088 A1* | 10/2002 | Sakaguchi ............ B01D 15/00 210/671 |
| 2003/0021760 A1 | 1/2003 | Kumar et al. |
| 2003/0053980 A1 | 3/2003 | Dodd et al. |
| 2004/0185011 A1 | 9/2004 | Alexander |
| 2005/0152851 A1 | 7/2005 | Kaminski |
| 2006/0024245 A1 | 2/2006 | Gebreselassie et al. |
| 2009/0155190 A1 | 6/2009 | Gebreselassie et al. |
| 2010/0061941 A1 | 3/2010 | Gebreselassie |
| 2011/0027328 A1 | 2/2011 | Baig et al. |
| 2011/0053826 A1 | 3/2011 | Wise |
| 2011/0262507 A1 | 10/2011 | Spring |
| 2013/0111682 A1 | 5/2013 | Pung |
| 2013/0302385 A1 | 11/2013 | Muenz et al. |
| 2014/0289984 A1 | 10/2014 | Vetter |
| 2015/0196185 A1 | 7/2015 | Fiske |
| 2015/0313803 A1 | 11/2015 | Lynch et al. |
| 2015/0313808 A1 | 11/2015 | Lynch et al. |
| 2016/0051684 A1 | 2/2016 | Wang |
| 2016/0120771 A1 | 5/2016 | Simonet et al. |
| 2016/0346175 A1 | 12/2016 | Sasik et al. |
| 2018/0127692 A1 | 5/2018 | Coope-epstein et al. |
| 2019/0160022 A1 | 5/2019 | Chiou |
| 2019/0298625 A1 | 10/2019 | Hilliard, Jr. et al. |
| 2019/0343732 A1 | 11/2019 | Mao |
| 2020/0000693 A1 | 1/2020 | Traynor et al. |
| 2021/0007940 A1 | 1/2021 | Swartz et al. |

FOREIGN PATENT DOCUMENTS

| | | |
|---|---|---|
| DE | 202007001353 U1 | 5/2007 |
| EP | 0916722 A2 | 5/1999 |
| EP | 2465487 A2 | 6/2012 |
| EP | 2170257 B1 | 11/2012 |
| GB | 2221389 A | 2/1990 |
| WO | 9209679 A1 | 6/1992 |
| WO | 0196461 A1 | 12/2001 |
| WO | 03075735 A1 | 9/2003 |
| WO | 2007133265 A2 | 11/2007 |
| WO | 2009095891 A1 | 8/2009 |
| WO | 2010060653 A2 | 6/2010 |
| WO | 2014124066 A1 | 8/2014 |

OTHER PUBLICATIONS

U.S. Unpublished U.S. Appl. No. 17/485,906, filed Sep. 27, 2021, to first inventor et al.
PCT Search Report and Written Opinion for PCT/US2021/026299 dated Jul. 30, 2021.
All Office Actions, U.S. Appl. No. 17/225,151.
All Office Actions, U.S. Appl. No. 17/225,153.
All Office Actions, U.S. Appl. No. 17/225,176.
All Office Actions, U.S. Appl. No. 17/225,218.
Clinton D. Stevenson, et al.,"Capillary Pressure as Related to Water Holding in Polyacrylamide and Chicken Protein Gels", Journal of Food Science, vol. 78, Nr. 2, dated 2013,pp. C145-C151.
F. V. Ryer, Oil & Soap, "Research Laboratory, Lever Brothers Company Cambridge, Massachusetts", dated Oct. 1946, pp. 310-313.
F. V. Ryer, et al. Growing Single Crystals, "A Method of Growing Single Crystals Of Sodium Stearate And Sodium Palmitate", dated Feb. 4, 1944, pp. 154-158.
Marc N. G. de Mul, et al. Langmuir 2000, "Solution Phase Behavior and Solid Phase Structure of Long-Chain Sodium Soap Mixtures", vol. 16, No. 22, dated 2000, pp. 8276-8284.
Masao Sambuichi, et al. Dewatering Of Gels, "Filtration, Food Chemical Engineering, Solid Liquid Separation, Dewatering, Expression, Gel", Journal of Chemical Engineering of Japan, vol. 27, No. 5, dated 1994, pp. 616-620.
Matthew L Lynch, Acid-soaps, "The study of acid-soap crystals has resulted in many conflicting data", Current Opinion in Colloid & Interface Science, dated 1997,pp. 495-500.
All Office Actions; U.S. Appl. No. 18/450,176, filed Aug. 15, 2023.
U.S. Unpublished U.S. Appl. No. 18/450,176, filed Aug. 15, 2023, to Matthew Lawrence Lynch et al.

(56) References Cited

OTHER PUBLICATIONS

All Office Actions, U.S. Appl. No. 17/196,379, filing date: Mar. 9, 2021.
All Office Actions, U.S. Appl. No. 17/225,146, filing date: Apr. 8, 2021.
All Office Actions, U.S. Appl. No. 17/225,149, filing date: Apr. 8, 2021.
All Office Actions, U.S. Appl. No. 17/225,150, filing date: Apr. 8, 2021.
Matthew L. Lynch, et al. Acid-soap crystals, "Spectroscopic and Thermal Characterization of 1:2 Sodium Soap/Fatty Acid Acid-Soap Crystals", J. Phys. Chem., vol. 100, No. 1, 1996, pp. 357-361.
Matthew L. Lynch, Structure of Fatty Acid-Soap Crystals, Intermolecular Interactions and the Structure of Fatty Acid-Soap Crystals, J. Phys. Chem. B, vol. 105, No. 2, dated 2001, pp. 552-561.
Theodore P. Labuza, et al., "Measurement Of Gel Water-Binding Capacity By Capillary Suction Potential", Journal of Food Science, vol. 43, dated 1978, pp. 1264-1269.
U.S. Unpublished U.S. Appl. No. 17/196,379, filed Mar. 9, 2021, to first inventor Geoffrey Marc Wise.
U.S. Unpublished U.S. Appl. No. 17/225,150, filed Apr. 8, 2021, to first inventor Matthew Lawrence Lynch et al.
U.S. Unpublished U.S. Appl. No. 17/225,218, filed Apr. 8, 2021, to first inventor Matthew Lawrence Lynch et al.
U.S. Unpublished U.S. Appl. No. 17/225,147, filed Apr. 8, 2021, to first inventor Matthew Lawrence Lynch et al.
U.S. Unpublished U.S. Appl. No. 17/225,149, filed Apr. 8, 2021, to first inventor Matthew Lawrence Lynch et al.
U.S. Unpublished U.S. Appl. No. 17/225,151, filed Apr. 8, 2021, to first inventor Matthew Lawrence Lynch et al.
U.S. Unpublished U.S. Appl. No. 17/225,153, filed Apr. 8, 2021, to first inventor Matthew Lawrence Lynch et al.
U.S. Unpublished U.S. Appl. No. 17/225,176, filed Apr. 8, 2021, to first inventor Matthew Lawrence Lynch et al.
Robert B Saper et al., "An Essential Micronutrient", vol. 79, No. 9, dated May 1, 2009, pp. 768-772.

* cited by examiner

RHEOLOGICAL SOLID COMPOSITION FOR USE IN PERSONAL CARE COMPOSITIONS

FIELD OF THE INVENTION

Personal care rheological solid composition comprising more than about 80% water having a crystallizing agent with an elongated, fiber-like crystal habit. Wherein the personal care rheological solid composition allows for a unique skin feel "crunch" and/or glide when rubbed on the skin providing an enhanced evaporative cooling for a refreshing/cooling sensation, even in the absence of sensate; and a low residue on skin and wherein the rheological solid also exhibits properties of sufficient firmness, aqueous phase expression and thermal stability critical for practical commercial viability.

BACKGROUND OF THE INVENTION

Conventional high-water containing compositions, such as rheological solid compositions, lack one or more desirable properties, for example—sufficient firmness, aqueous phase expression and thermal stability, particularly those comprising sodium carboxylate-based crystallizing agents. For instance, to produce a firm rheological solid composition using sodium stearate (C18) as a gelling agent in conventional soap-type deodorant gel-sticks requires the inclusion of high levels of polyols (e.g. propylene glycol and glycerin), as a solubility aid for the sodium stearate during processing, even at high process temperatures. Typical compositions include about 50% propylene glycol, 25% glycerin and only 25% water (EP2170257 and EP2465487). However, the addition of these processing aids eliminates the crunch and mutes the glide feel and cooling sensation of the solid gel stick. Even using lower amounts of a polyol compound, such as a glycol or a polyglycol, about 4% or more of sodium stearate (C18) is needed to provide sufficient firmness which then can result in higher amounts of gelling agent being left on the skin (U.S. Pat. No. 4,322,400). Traditional soap bars are comprised of similar gelling agents, but are far too concentrated in sodium carboxylate to effectively allow for aqueous phase expression with compression. Thermal stability is compromised in compositions when a gelling agent that is too soluble is added (U.S. Pat. No. 5,340,492); in this instance, the thermal stability temperature of the composition is too low to effectively survive reliably on the shelf life or in the supply chain.

There is a consumer demand for products that offer moisturization, improved health, and improved appearance to the skin when applied. Current product offerings are often liquids or creams which consumers often find messy and inconvenient to apply, both because of the undesired residue left on hands and often clothes and is awkward to apply to sensitive areas such as the face. The current products in stick form are often based on waxy- or oily-based formations and—while firm, tend to be greasy. Consumers need a stick product to moisturize, cool, and soothe the skin, that is not greasy.

What is needed is a rheological solid composition that leaves little residue and has sufficient firmness, aqueous phase expression, and thermal stability. The present invention of a self-supporting structure comprising a crystalline mesh of a relatively rigid, framework of fiber-like crystalline particles, which if compressed, provides the properties of low residue, sufficient firmness, thermal stability, and aqueous phase expression.

SUMMARY OF THE INVENTION

A personal care rheological solid composition is provided that comprises crystallizing agent and aqueous phase; wherein, the personal care rheological solid composition has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 100 J m−3 to about 8,000 J m−3 as determined by the AQUEOUS PHASE EXPRESSION TEST METHOD; and wherein the crystallizing agent is a salt of fatty acids containing from about 13 to about 20 carbon atoms.

A method of producing a personal care rheological solid composition is provided that comprises providing water; providing a crystallizing agent that is a salt of fatty acids containing from about 13 to about 20 carbon atoms; providing NaCl; wherein the NaCl is about 10% or less per weight percentage of the personal care rheological solid composition; mixing the water, crystallizing agent, and NaCl; producing a personal care rheological solid composition wherein, the personal care rheological solid composition, has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 300 J m−3 to about 9,000 J m−3 as determined by the AQUEOUS PHASE EXPRESSION TEST METHOD.

A method of producing a personal care rheological solid composition is provided that comprises providing water; providing a crystallizing agent that is a salt of fatty acids containing from about 13 to about 20 carbon atoms; mixing the water and crystallizing agent to produce a personal care rheological solid composition; adding NaCl to the personal care rheological solid composition; wherein, the personal care rheological solid composition after addition of the NaCl, has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 300 J m−3 to about 9,000 J m−3 as determined by the AQUEOUS PHASE EXPRESSION TEST METHOD.

A personal care rheological solid composition is provided that comprises crystallizing agent and aqueous phase; wherein, the personal care rheological solid composition has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 100 J m−3 to about 8,000 J m−3 as determined by the AQUEOUS PHASE EXPRESSION TEST METHOD; and wherein the crystallizing agent is a salt of fatty acids containing from about 13 to about 16 carbon atoms.

A method of producing a personal care rheological solid composition is provided that comprises providing water; providing a crystallizing agent that is a salt of fatty acids containing from about 13 to about 16 carbon atoms; providing NaCl; wherein the NaCl is about 10% or less per weight percentage of the personal care rheological solid composition; mixing the water, crystallizing agent, and NaCl; producing a personal care rheological solid composition wherein, the personal care rheological solid composition, has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 300 J m-3 to about 9,000 J m-3 as determined by the AQUEOUS PHASE EXPRESSION TEST METHOD.

A method of producing a personal care rheological solid composition is provided that comprises providing water; providing a crystallizing agent that is a salt of fatty acids containing from about 13 to about 16 carbon atoms; mixing the water and crystallizing agent to produce a personal care rheological solid composition; adding NaCl to the personal care rheological solid composition; wherein, the personal care rheological solid composition after addition of the NaCl, has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 300 J m-3 to about 9,000 J m-3 as determined by the AQUEOUS PHASE EXPRESSION TEST METHOD.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

The present invention includes a personal care rheological solid composition comprising a crystalline mesh. The crystalline mesh ("mesh") comprises a relatively rigid, three-dimensional, interlocking crystalline skeleton framework of fiber-like crystalline particles (formed from crystallizing agents), having voids or openings containing aqueous solution and optionally one or more actives. The mesh provides a self-supporting structure, such that a personal care rheological solid composition may 'stand on its own' when resting on a surface. If compressed above a critical stress, the mesh allows the personal care rheological solid composition to express the entrapped aqueous phase, and optionally water soluble actives. The personal care rheological solid compositions of the present invention include crystallizing agent(s), aqueous phase, and optionally a suspension agent and/or active (which may be insoluble) and may be combined with a device to enable application.

Figure 3:
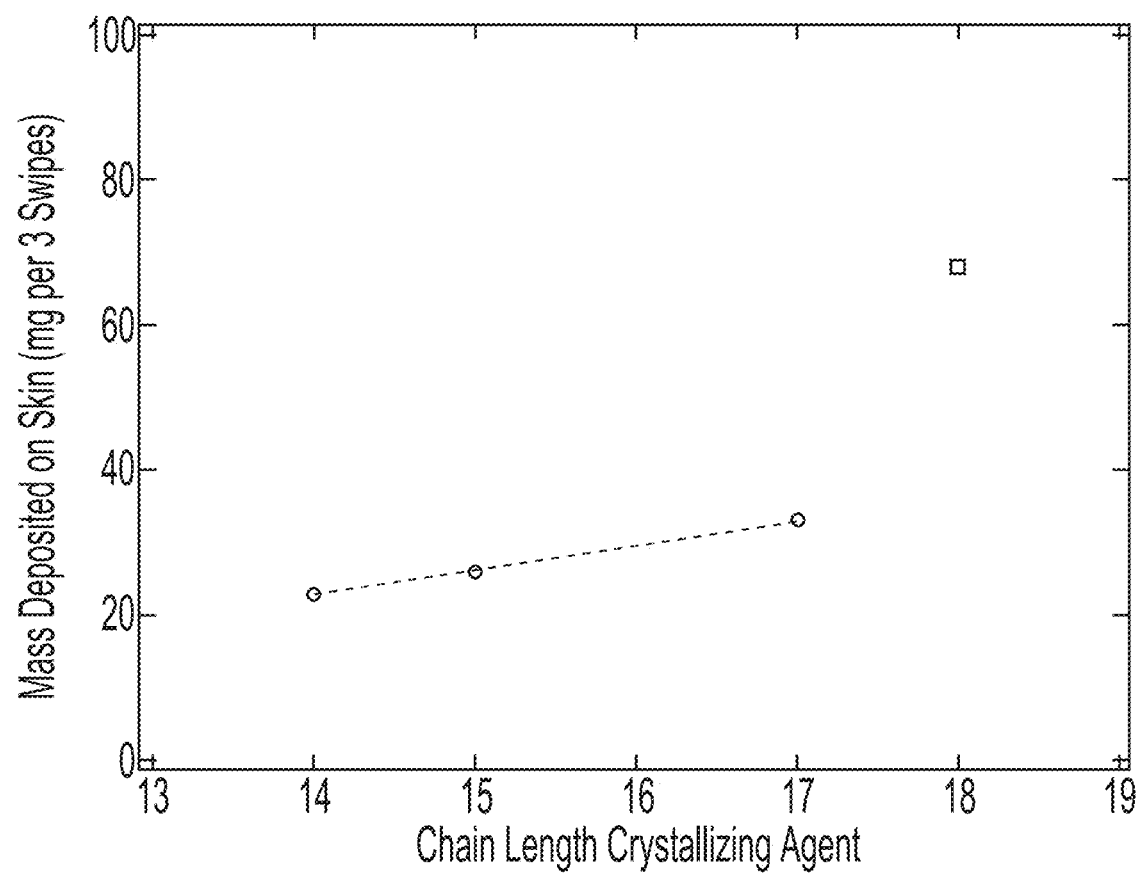
FIG. 3. Graph illustrating Composition Transferred to Skin

It is surprising that it is possible to prepare personal care rheological solid compositions that exhibit low residue, sufficient firmness, aqueous phase expression, and thermal stability. Not wishing to be bound by theory, it is believed that sodium carboxylates of a sufficiently low chain length, such as from C13 to C20, in particular those with a chain length of from about C13 to about C16, present in high-water compositions (e.g. above about 80%), with the correct chain length purity and prepared under viable and practical process condition may form elongated, fiber-like crystal habits making these compositions particularly useful. These molecules have an ideal hydrophilic-hydrophobic balance between the head group and fatty chain to grow optimal crystal habits; these molecules also have a Krafft Temperature significantly below the viable and practical process temperatures, to grow optimal crystal habits. Shorter chain sodium carboxylates (about C13 to about C20, in particular about C13 to about C16) result in personal care rheological solid compositions comprising a crystalline mesh, even at very low concentrations of sodium carboxylates, that are firm (resistant to compression stress) and deposit very little residual solid material upon a surface contacted by the rheological solid (resistant to shear stress) (FIG. 3). Firmness may be achieved by carefully adjusting the concentration and chain length distribution of the crystallizing agent. Aqueous phase expression may be achieved from these rheological solid structures, by compression above a yield behavior that breaks the mesh structure allowing water and any dissolved actives to flow from the composition. One skilled in the art recognizes this as a plastic deformation of the mesh structure. This stands in contrast to other gelling agents like gelatin, that can be formulated at very high-water concentrations but do not express water with compression. Thermal Stability may be achieved by ensuring the proper chain length and chain length distributions to ensure the mesh does not solubilize until heated above 40° C. This is an important property in relation to the shelf-life and supply chain for consumer products. Addition of sodium chloride can be used to increase the thermal stability of the composition but should be added correctly to ensure the proper formation of the supporting mesh. These discovered design elements stand in contrast to compositions prepared with too-soluble a gelling agent to be practically thermal stable. Finally, in embodiments personal care rheological solid compositions are prepared by cooling the mixture largely quiescently, in contrast to freezer or other mechanically invasive processes. Not wishing to be bound by theory, quiescent processes allow the formation of very large and efficient fibrous crystals rather than smaller less efficient crystals that are particularly subject to residual solid material deposition during use.

Personal care rheological solid compositions of the present invention can provide both short-term and long-term cooling effects when applied to the skin. This invention includes personal care rheological solid compositions that provide cooling benefits enabling short-term evaporative cooling from mixtures of water and ethanol and long-term cooling effects from sensates. Certain embodiments may be in the form of a stick for discreet use and in an aqueous chassis to eliminate greasy feel and make them safe for clothes.

Many consumers desire products that provide short-term cooling for instant relief coupled with long-term cooling for sustained relief, all done in a discreet way with non-greasy feel to the skin and protection to clothes. As one example, menopausal women may experience 'hot flashes' and for these consumers short-term cooling relieves immediate symptoms and the long-term cooling provides sustained confidence. As another example, athletes may be very hot after a work-out and for these consumers the short-term cooling returns the athlete to base conditions and the long-terms cooling provide sustained refreshment. Sprays offer short-term benefits either by cooling with compressed gas or by spritzing with water. They offer short-term benefits, but no long-term benefits and are not discreet in implementation. There are also products that offer long-term cooling benefits, most oil-based sensates, that enable a lasting cooling sensation but typically have greasy feeling and potential for staining clothes. Consumers need a product that offers both short-term and long-term cooling and relief, that is non-greasy feeling, discreet and safe for clothes.

Crystallizing Agent(s)

Figure 1:
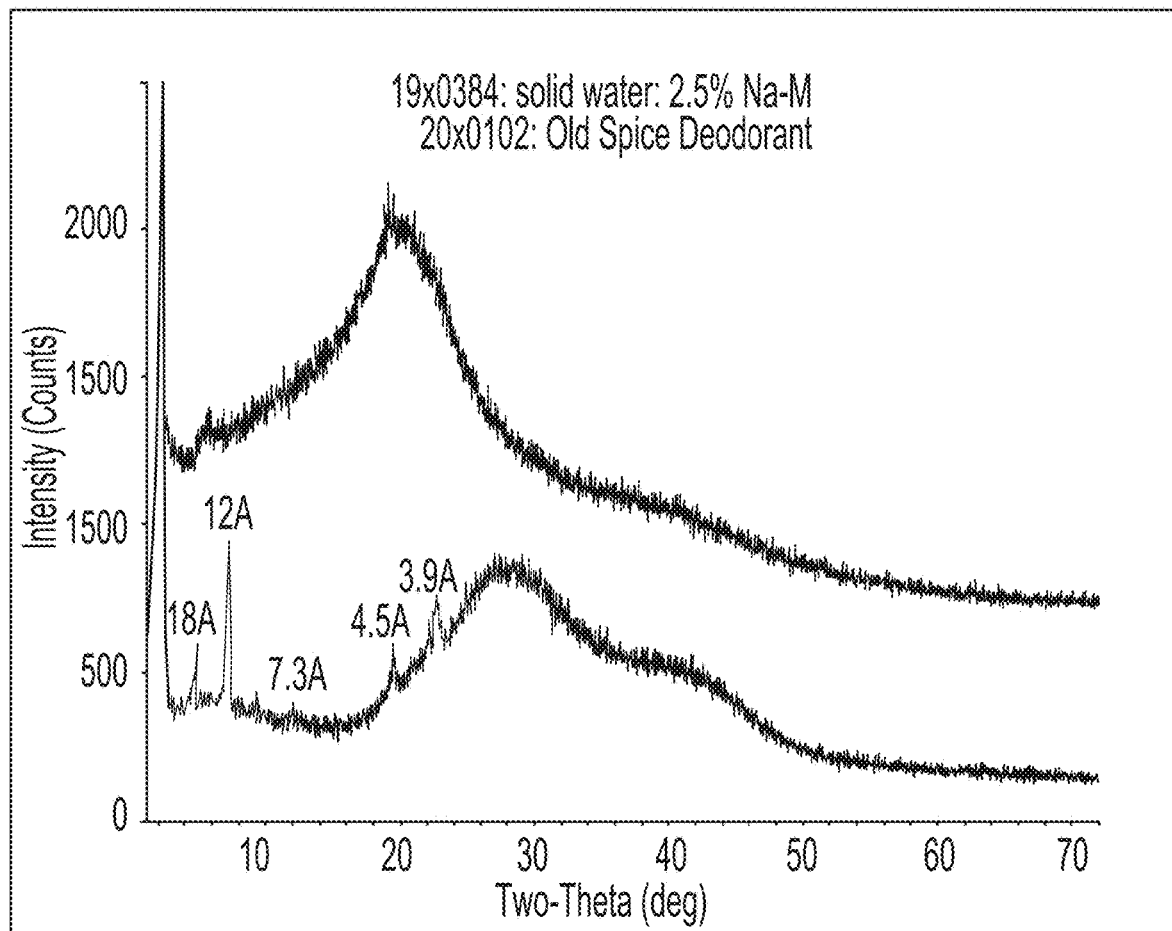
FIG. 1. X-ray Diffraction Pattern

In the present invention the mesh of a personal care rheological solid composition includes fiber-like crystalline particles formed from crystallizing agents; wherein "Crystallizing agent" as used herein includes sodium salts of fatty acids with shorter chain length (from about C13 to about C20 or from about C13 to about C18 or from about C13 to about C16 or from about C13 to about C14), such as sodium tridecanoate, sodium pentadecanoate, sodium heptadecanoate, or sodium palmitate (C16). Commercial sources of crystallizing agent usually comprise complicated mixtures of molecules, often with chain lengths between C10 to C22. The personal care rheological solid compositions are best achieved with a 'narrow blend'—or distribution of crystallizing agent chain lengths, further best achieved with blends in the absence of very short chain lengths (C12 or shorter) and measurable amounts of unsaturation on the chains of the fatty acid sodium salts, and best achieved with a single chain length between C13 to C20, coupled with controlled crystallizing processing. Accordingly, personal care rheological solid compositions are best achieved when the blend of the chain length distribution is preferably greater than about Po>0.3, more preferably about Po>0.5, more preferably about Po>0.6, more preferably about Po>0.7 and most preferably about Po>0.8, as determined by the BLEND TEST METHOD. One skilled in the art, recognizes crystalline particles as exhibiting sharp scattering peaks between 0.25-60 deg. 2θ in powdered x-ray diffraction measurements. This is in sharp contrast to compositions in which these materials are used as gelling agents, which show broad amorphic scattering peaks emanating from poorly formed solids which lack the long-range order of crystalline solids (FIG. 1).

Figure 2:
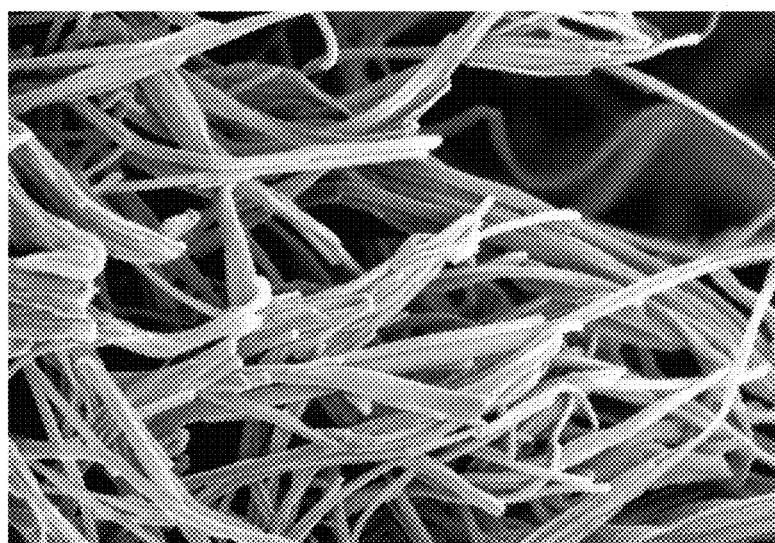
FIG. 2. SEM of Interlocking Mesh

Personal care rheological solid compositions comprise greater than about 80% water and are 'structured' by a mesh of interlocking, fiber-like crystalline particles of mostly single-chain length, as described above, see (FIG. 2). The term 'fiber-like crystalline particle' refers to a particle in which the length of the particle in the direction of its longest axis is greater than 10× the length of the particle in any orthogonal direction. The fiber-like crystalline particles produce a mesh at very low concentrations (~0.5 wt %) which creates a solid that yields only with a minimum applied stress—i.e.

rheological solid. In embodiments comprising suspension agents, the suspension agent(s), insoluble active(s) and aqueous phase (water) primarily reside in the open spaces of the mesh. In preparing these compositions, the crystallization agent is dissolved in water using heat. The fiber-like crystalline particles form into the mesh as the mixture cools over minutes to hours. Not wishing to be bound by theory, but the suspension agents—such as polymer gums, clay particles and hydrophobic fat particles, prevent the insoluble active agents from creaming or sedimentation, during the formation of the mesh. The aqueous phase primarily resides in the open spaces of the mesh. In preparing these compositions, the crystallizing agent is dissolved in aqueous phase using heat. The fiber-like crystalline particles form into the mesh as the mixture cools over minutes to hours.

Such compositions exhibit three properties used to make effective consumer product for envisioned applications:

Aqueous Phase Expression

Aqueous phase expression is an important property for consumer applications in the present invention, expressed in work to express water per unit volume, where preferred compositions are between 300 J m−3 and about 9,000 J m−3, more preferably between 1,000 J m−3 and about 8,000 J m−3, more preferably between 2,000 J m−3 and about 7,000 J m−3 and most preferably between 2,500 J m−3 and about 6,000 J m−3, as determined by the AQUEOUS PHASE EXPRESSION TEST METHOD. These limits allow for viable product compositions that—for example, provide evaporative and/or sensate-based cooling when the composition is applied to the skin and cleaning when applied to a hard surface. These work limits are in contrast to bar soaps and deodorant sticks that do not express aqueous phase when compressed. These work limits are also in contrast to gelatins that likewise do not express water when compressed. So, it is surprising that high-water compositions can be created with these materials, that express aqueous phase with compression. Not wishing to be bound by theory, it is believed this a result of a network of crystalline materials that break up during the application of sufficient stress—releasing the aqueous phase with no uptake when the compression is released.

Firmness

Firmness should be agreeable to consumer applications, in forming a structured personal care rheological solid composition, with preferred embodiments between about 0.5 N to about 25.0 N, more preferably between 1.0 N to about 20.0 N, more preferably between 3.0 N to about 15.0 N and most preferably between 5.0 N and about 10.0 N. These firmness values allow for viable product compositions that may retain their shape when resting on a surface, and as such are useful as a rheological solid stick to provide a dry-to-the-touch but wet-to-the-push properties. The firmness values are significantly softer than bar soaps and deodorants, which exceed these values. So, it is surprising that high-water compositions can be created that remain as personal care rheological solid compositions with between about 0.25 wt % to about 10 wt % crystallizing agent, more preferably between about 0.5 wt % to about 7 wt % crystallizing agent and most preferably between about 1 wt % to about 5 wt % crystallizing agent. Not wishing to be bound by theory, it is believed this a result of crystallizing agent materials creating the interlocking mesh that provides sufficient firmness.

Thermal Stability

Thermal stability is used to ensure that the structured personal care rheological solid composition can be delivered as intended to the consumer through the supply chain, preferably with thermal stability greater than about 40° C., more preferably greater than about 45° C. and most preferably greater than about 50° C., as determined by the THERMAL STABILITY TEST METHOD. Creating compositions with acceptable thermal stability is difficult, as it may vary unpredictably with concentration of the crystallizing agent and soluble active agent(s). Not wishing to be bound by theory, thermal stability results from the insolubility of the crystallizing agent in the aqueous phase. Conversely, thermal instability is thought to result from complete solubilization of the crystallizing agent that comprised the mesh.

Chain Length Blends

Effective chain length blends allow the creation of effective mesh microstructures in personal care rheological solid compositions. In fact, adhoc (or informed selection) of crystallizing agents often leads to liquid or very soft compositions. The crystallizing agent may comprise a mixture of sodium carboxylate molecules, where each molecule has a specific chain length. For example, sodium stearate has a chain length of 18, sodium oleate has a chain length of 18:1 (where the 1 reflects a double bond in the chain), sodium palmitate has a chain length of 16, and so on. The chain length distribution—or the quantitative weight fraction of each chain length in the crystallizing agent, can be determined by the BLEND TEST METHOD, as described below. Commercial sources of crystallizing agent usually comprise complicated mixtures of molecules, often with chain lengths between 10 to 22.

Personal care rheological solid compositions of the present invention have preferred chain length blends, as described by 'Optimal Purity' (Po) and 'Single Purity' (Ps), determined by the BLEND TEST METHOD. Sodium carboxylate crystallizing agents can have an 'Optimal Chain Length' of between 13 to 22 carbons and can be used alone or combined to form mesh structures that satisfy all three performance criteria of a personal care rheological solid composition. Not wishing to be bound by theory, it is believed that these chain length molecules (13 to 20, in particular 13 to 16) have an optimal hydrophilic-hydrophobic balance and a solubilization temperature (e.g. Krafft Temperature) sufficiently below a viable and practical process temperature, that they can pack into crystals efficiently. When present in compositions alone or in some combinations with 'optimal chain length' molecules, they do not form personal care rheological solid composition that meet the required performance criteria. Accordingly, inventive compositions should have the proper purity of crystallizing agent molecules, to ensure the proper properties of the personal care rheological solid composition. Po describes the total weight fraction of optimal chain length molecules of crystallizing agent to the total weight of crystallizing agent molecules, that is preferably Po>0.4, more preferably Po>0.6, more preferably Po>0.8 and most preferably Po>0.90. Ps describes the total weight fraction of the most common chain length molecule in the crystallizing agent to the total weight of crystallizing agent, that is preferably Ps>0.5, more preferably Ps>0.6, more preferably Ps>0.7, more preferably Ps>0.9.

Suspension Agent(s)

The suspension agent prevents the separation of insoluble actives in the preparation of the personal care rheological solid composition. Inventive compositions are heated until the crystallization agent is dissolved leaving a dispersed active in a low viscosity fluid. When the compositions are cooled, the crystallization agent begins to form fiber-like crystalline particles which weave together into the mesh which eventually traps the actives. This process can take minutes to hours. Not wishing to be bound by theory, it is believed that that suspension agents increase viscosity or create a yield stress that holds the actives from creaming or sedimenting during the crystallization of the crystallizing agent and formation of the mesh. Preferred suspension agents are effective at low concentrations, to prevent potential negative effects on the mesh and performance of the consumer product. Preferred levels are below 2 wt %, more preferred below 1 wt %, more preferred below 0.5 wt % and most preferred below 0.1 wt %. Suitable suspension agents include gums, polymers, microfiber particles and clay particles, and unexpectedly must be selected for a composition, such that their addition does not have a negative effect on the mesh. For example, the use of gums can weaken the mesh structure relative to compositions that do not contain gums requiring an increase in the amount of crystallize agent (Example 2). As another example, use of clays (Example 10) and microfibers (Example 9) can be rendered ineffective with the addition of sodium chloride.

Gums

The personal care rheological solid composition includes at least one suspension agent to keep insoluble materials (i.e. solids or oils) suspended during preparation. The suspension agent may include one or more biopolymers. Non-limiting examples of such biopolymers include polysaccharides such as polymers of glucose, fructose, galactose, mannose, rhamnose, glucuronic acid, and mixtures thereof.

The suspension agent may be in the form of a polysaccharide or mixture of polysaccharides. Preferable polysaccharide suspension agents include xanthan gum, glucomannan, galactomannan, and combinations thereof. The glucomannan may be derived from a natural gum such as konjac gum. The galactomannan may be derived from naturals gums such as locust bean gum. Polysaccharide suspension agents may also include carrageenan. Suspension agent gums may be modified such as by deacetylation.

The personal care rheological solid composition may include a polysaccharide suspension agent system comprising at least two polysaccharides, such as a first polysaccharide and a second polysaccharide. The first polysaccharide may be xanthan gum. The second polysaccharide may be selected from the group consisting of glucomannan, galactomannan, and combinations thereof. The second polysaccharide may be selected from the group consisting of konjac gum, locust bean gum, and tara bean combinations thereof.

Preferably, the first polysaccharide is xanthan gum and the second polysaccharide is konjac gum.

The first polysaccharide may be present at a level of greater than about 10 wt. % and less than about 100 wt. %, alternatively about 40 wt. % to about 90 wt. %, alternatively about 40 wt. % to about 60 wt. %, by weight of the polysaccharide suspension agent system.

The second polysaccharide may be present at a level of about 0 wt. % to about 90 wt. %, alternatively about 60 wt. % to about 10 wt. %, alternatively about 60 wt. % to about 40 wt. %, by weight of the polysaccharide suspension agent system.

The total concentration of polysaccharide present in the personal care rheological solid composition may be between about 0.01-1.0 wt. %, or more preferably between about 0.03-1.0 wt. %, or more preferably between about 0.05-0.8 wt. %, more preferably between 0.07-0.75 wt. %, and most preferably between 0.09-0.5 wt. %. Without wishing to be bound by theory, it is believed that minimizing the total polysaccharide level in the composition ensures stability of the dispersed active agents during preparation while minimizing the effect of the suspension agent on the mesh structure.

The polysaccharide suspension agent system may have a weight-average molecular weight in the range of about 10,000 Daltons to about 15,000,000 Daltons, alternatively about 200,000 Daltons to about 10,000,000 Daltons, alternatively about 300,000 Daltons to about 6,000,000 Daltons, alternatively about 300,000 Daltons to about 500,000 Daltons.

The polysaccharide suspension agent system may be characterized by the average ratio of acetylation wherein the average ratio of acetylation is the number of acetylated hydroxyl groups in the polysaccharide divided by the number of free hydroxyl groups in the polysaccharide. The average ratio of acetylation may be in the range of about 2.0 to about 0.5, preferably in the range of about 1.5 to about 0.5.

Clays

In the present disclosure, a suspending agent may be used to provide viscosity and thixotropic properties to the composition, so that the suspended active agent particles are prevented from creaming or settling during preparation. In one or more embodiments, the suspending agent may be a mineral clay mixture and more particularly an organophilic mineral clay mixture. In one or more embodiments, the mineral clay mixture may be treated with alkyl quaternary ammonium compounds in order to render the mineral clay mixture hydrophobic; such clays may also be termed organophilic. In one or more embodiments, the mineral clay mixtures comprise: a mineral clay (a) comprising 50 to 95 wt. %, based on the weight of the mineral clay mixture, or 60 to 95 wt. %, or 70 to 90 wt. % of a mineral clay selected from the group including sepiolite, palygorskite and mixtures of sepiolite and palygorskite; and a mineral clay (b) comprising the balance by weight of the mineral clay mixture, of a smectite. In one or more embodiments, the smectite may be a natural or synthetic clay mineral selected from the group including hectorite, laponite, montmorillonite, bentonite, beidelite, saponite, stevensite and mixtures thereof. Suitable clays include Laponite from the Garamite line of products available from BYK Additives, (Gonzalez, Tex.).

Microfibers

Any microcrystalline cellulose may be employed in the compositions of the present invention. Suitable feedstocks include, for example, wood pulp such as bleached sulfite and sulfate pulps, corn husks, bagasse, straw, cotton, cotton linters, flax, kemp, ramie, fermented cellulose, etc. The amounts of microcrystalline cellulose and hydrocolloid may be varied over a wide range depending upon the properties desired in the final composition. Suitable microfibers include Rheocrysta c-2sp (WASE COSFA USA, Inc.)

Insoluble Active(s)

The personal care rheological solid composition may include one or more insoluble active particles besides the fiber-like crystal particles that comprise the mesh. As used herein, an "insoluble active particle" comprises at least a portion of a solid, a semi-solid, or liquid material, including some amount of insoluble active. The insoluble active particles may take various different forms, for example the insoluble active particles may be 100 wt. % solid or may be hollow. The insoluble active particles may include, for example, mesoporous particles, activated carbon, zeolites, benefit agent delivery particle, waxes, insoluble oils, hydrogel, and/or ground nutshells.

The personal care rheological solid composition may include one or more types of insoluble active particles, for example, two insoluble active particles types, wherein one of the first or second insoluble active particles (a) is made of a different material than the other; (b) has a wall that includes a different amount of wall material or monomer than the other; or (c) contains a different amount perfume oil ingredient than the other; (d) contains a different perfume oil; (e) has a wall that is cured at a different temperature; (f) contains a perfume oil having a different c Log P value; (g) contains a perfume oil having a different volatility; (h) contains a perfume oil having a different boiling point; (i) has a wall made with a different weight ratio of wall materials; (j) has a wall that is cured for different cure time; and (k) has a wall that is heated at a different rate.

The plurality of insoluble active agent particles may have diameter less than 500 um, less than 400 um, less than 300 um, less than 200 um and less than 100 um. One skilled in the art recognizes that the ability to suspend particles is a function of the mean diameter of the particles (where larger particles are more difficult to suspend) and a function of the total amount of the particles (where large amounts of particles are more difficult to suspend).

To the former, one skilled in the art further recognizes that the concentration of the suspension agent with a given insoluble active agent may have to be increased to accommodate larger insoluble active particles. It is generally preferred to minimize the amount of suspension agent (e.g. Example 2) so that smaller active agent particles are preferred. To the latter, one skilled in the art further recognizes that the concentration of the suspension agent with a given insoluble active agent may have to be increased to accommodate larger amounts of insoluble active particles.

Encapsulated Insoluble Benefit Agent

The insoluble active particle may include a wall material that encapsulates an insoluble active. The insoluble active may be selected from the group consisting of: perfume compositions, perfume raw materials, perfume, skin coolants, vitamins, sunscreens, antioxidants, glycerin, chelating agents, colorants, antioxidants, sanitization agents, disinfecting agents, germ control agents, antiviral agents, antifoaming agents, UV protection agents, skin care agents, and natural actives, antibacterial actives, antiperspirant actives, activators, and enzymes. As used herein, a "perfume raw material" refers to one or more of the following ingredients: fragrant essential oils; aroma compounds; pro-perfumes; materials supplied with the fragrant essential oils, aroma compounds, and/or pro-perfumes, including stabilizers, diluents, processing agents, and contaminants; and any material that commonly accompanies fragrant essential oils, aroma compounds, and/or pro-perfumes.

The wall material of the insoluble active particle may comprise melamine, polyacrylamide, silicones, silica, polystyrene, polyurea, polyurethanes, polyacrylate based materials, polyacrylate ester-based materials, gelatine, styrene malic anhydride, polyamides, aromatic alcohols, polyvinyl alcohol and mixtures thereof. The melamine wall material may comprise melamine crosslinked with formaldehyde, melamine-dimethoxyethanol crosslinked with formaldehyde, and mixtures thereof. The polystyrene wall material may comprise polyestyrene cross-linked with divinylbenzene. The polyurea wall material may comprise urea cross-linked with formaldehyde, urea crosslinked with gluteraldehyde, polyisocyanate reacted with a polyamine, a polyamine reacted with an aldehyde and mixtures thereof. The polyacrylate based wall materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof.

The polyacrylate ester-based wall materials may comprise polyacrylate esters formed by alkyl and/or glycidyl esters of acrylic acid and/or methacrylic acid, acrylic acid esters and/or methacrylic acid esters which carry hydroxyl and/or carboxy groups, and allylgluconamide, and mixtures thereof.

The aromatic alcohol-based wall material may comprise aryloxyalkanols, arylalkanols and oligoalkanolarylethers. It may also comprise aromatic compounds with at least one free hydroxyl-group, especially preferred at least two free hydroxy groups that are directly aromatically coupled, wherein it is especially preferred if at least two free hydroxy-groups are coupled directly to an aromatic ring, and more especially preferred, positioned relative to each other in meta position. It is preferred that the aromatic alcohols are selected from phenols, cresols (o-, m-, and p-cresol), naphthols (alpha and beta-naphthol) and thymol, as well as ethylphenols, propylphenols, fluorphenols and methoxyphenols.

The polyurea based wall material may comprise a polyisocyanate. The polyisocyanate may be an aromatic polyisocyanate containing a phenyl, a toluoyl, a xylyl, a naphthyl or a diphenyl moiety (e.g., a polyisocyanurate of toluene diisocyanate, a trimethylol propane-adduct of toluene diisocyanate or a trimethylol propane-adduct of xylylene diisocyanate), an aliphatic polyisocyanate (e.g., a trimer of hexamethylene diisocyanate, a trimer of isophorone diisocyanate and a biuret of hexamethylene diisocyanate), or a mixture thereof (e.g., a mixture of a biuret of hexamethylene diisocyanate and a trimethylol propane-adduct of xylylene diisocyanate). In still other embodiments, the polyisocyanate may be cross-linked, the cross-linking agent being a polyamine (e.g., diethylenetriamine, bis(3-aminopropyl) amine, bis(hexanethylene)triamine, tris(2-aminoethyl) amine, triethylenetetramine, N,N'-bis(3-aminopropyl)-1,3-propanediamine, tetraethylenepentamine, pentaethylenehexamine, branched polyethylenimine, chitosan, nisin, gelatin, 1,3-diaminoguanidine monohydrochloride, 1,1-dimethylbiguanide hydrochloride, or guanidine carbonate).

The polyvinyl alcohol based wall material may comprise a crosslinked, hydrophobically modified polyvinyl alcohol, which comprises a crosslinking agent comprising i) a first dextran aldehyde having a molecular weight of from 2,000 to 50,000 Da; and ii) a second dextran aldehyde having a molecular weight of from greater than 50,000 to 2,000,000 Da.

Preferably, the insoluble active particle with perfume has a wall material comprising silica or a polymer of acrylic acid or derivatives thereof and a benefit agent comprising a perfume mixture.

With regards to insoluble active particles, the personal care rheological solid composition may contain from about 0.001 wt. % to about 20 wt. %, by weight of the personal care rheological solid composition, of benefit agent contained with the wall material of the benefit agent delivery particle. Or, the personal care rheological solid composition may contain from about 0.01 wt. % to about 10 wt. %, or most preferably from about 0.05 wt. % to about 5 wt. %, by weight of the personal care rheological solid composition, of benefit agent contained with the wall material of the insoluble active particle.

These walled particles may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof.

Unencapsulated Perfume

The personal care rheological solid composition may include unencapsulated perfume comprising one or more perfume raw materials that solely provide a hedonic benefit (i.e. that do not neutralize malodors yet provide a pleasant fragrance). Suitable perfumes are disclosed in U.S. Pat. No. 6,248,135. For example, the personal care rheological solid composition may include a mixture of volatile aldehydes for neutralizing a malodor and hedonic perfume aldehydes.

Where perfumes, other than the volatile aldehydes in the malodor control component, are formulated into the personal care rheological solid composition, the total amount of perfumes and volatile aldehydes may be from about 0.015 wt. % to about 2 wt. %, alternatively from about 0.01 wt. % to about 1.0 wt. %, alternatively from about 0.015 wt. % to about 0.5 wt. %, by weight of the personal care rheological solid composition.

Perfume Delivery Technologies

The personal care rheological solid compositions may comprise one or more perfume delivery technologies that stabilize and enhance the deposition and release of perfume ingredients from a treated substrate. Such perfume delivery technologies can also be used to increase the longevity of perfume release from the treated substrate. Perfume delivery technologies, methods of making certain perfume delivery technologies and the uses of such perfume delivery technologies are disclosed in US 2007/0275866 A1.

The personal care rheological solid compositions may comprise from about 0.001 wt. % to about 20 wt. %, or from about 0.01 wt. % to about 10 wt. %, or from about 0.05 wt. % to about 5 wt. %, or even from about 0.1 wt. % to about 0.5 wt. % by weight of the perfume delivery technology. In one aspect, the perfume delivery technologies may be selected from the group consisting of: pro-perfumes, polymer particles, soluble silicone, polymer assisted delivery, molecule assisted delivery, assisted delivery, amine assisted delivery, cyclodextrins, starch encapsulated accord, zeolite and inorganic carrier, and mixtures thereof.

The perfume delivery technology may comprise an amine reaction product (ARP) or a thio reaction product. One may also use "reactive" polymeric amines and or polymeric thiols in which the amine and/or thiol functionality is pre-reacted with one or more PRMs to form a reaction product. Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen and/or sulfur, for example oxygen, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

Essential and Natural Oils

The insoluble active particle may include individual of mixtures of essential and natural oils. The term "essential oils" as used herein refers to oils or extracts distilled or expressed from plants and constituents of these oils. Typical essential oils and their main constituents are those obtained for example from thyme (thymol, carvacrol), oregano (carvacrol, terpenes), lemon (limonene, terpinene, phellandrene, pinene, citral), lemongrass (citral, methylheptenone, citronellal, geraniol), orange flower (linalool, β-pinene, limonene), orange (limonene, citral), anise (anethole, safrol), clove (eugenol, eugenyl acetate, caryophyllene), rose (geraniol, citronellol), rosemary (borneol, bornyl esters, camphor), geranium (geraniol, citronellol, linalool), lavender (linalyl acetate, linalool), citronella (geraniol, citronellol, citronellal, camphene), eucalyptus (eucalyptol); peppermint (menthol, menthyl esters), spearmint (carvone, limonene, pinene); wintergreen (methyl salicylate), camphor (safrole, acetaldehyde, camphor), bay (eugenol, myrcene, chavicol), cinnamon (cinnamaldehyde, cinnamyl acetate, eugenol), tea tree (terpinen-4-ol, cineole), eucalyptus oil, nutmeg oil, turpentine oil and cedar leaf (α-thujone, β-thujone, fenchone). Essential oils are widely used in perfumery and as flavorings, medicine and solvents. Essential oils, their composition and production, are described in detail in Kirk-Othmer Encyclopedia of Chemical Technology, 4$^{th}$ Edition and in The Merck Index, 13$^{th}$ Edition.

Waxes and Oils

The insoluble active particle may include individual of mixtures of waxes and oils. The non-aqueous vehicle is generally any chemical in any physical form that does not contain water. The non-aqueous vehicle is selected from the group consisting of liquid petrolatum, petrolatum, mineral oil, glycerin, natural and synthetic oils, fats, silicone and silicone derivatives, polyvinylacetate, natural and synthetic waxes such as animal waxes like beeswax, lanolin and shellac, hydrocarbons, hydrocarbon derivatives, vegetable oil waxes such as carnauba, candelilla and bayberry wax, vegetable oils such as caprylic/capric triglycerides, in another embodiment is selected from the group consisting of liquid petrolatum, petrolatum, mineral oil, vegetable oils such as apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, and animal oil such as fish oil and oleic acid, and mixtures thereof; and in yet another embodiment is mineral oil.

Malodor Counteractants

The personal care rheological solid composition may include other malodor reducing technologies. This may include, without limitation, amine functional polymers, metal ions, cyclodextrins, cyclodextrin derivatives, polyols, oxidizing agents, activated carbon, zeolites, and combinations thereof.

Feel Modifiers

The personal care rheological solid composition may also include insoluble active agents designed to alter the feel properties of the composition when applied to surfaces, such as skin. This may include starches, e.g Talc, tapioca startch, rice starch, fumed silica (Aerosil 200), titanium dioxide, dimethicone, iron oxide, mica, charcoal, colloidal oatmeal, colloidal cellulose, kaolin, Skin Care Agents Skin care agents may be added to deliver a therapeutic and/or skin protective benefit. It will be recognized that of the numerous materials useful in the compositions delivered to skin, those that have been deemed safe and effective skin care agent and mixtures thereof are logical materials for use herein. Such materials include Category 1 actives as defined by the U.S. Food and Drug Administration's (FDA) Tentative Final Monograph on Skin Protectant Drug Products for Over-the-Counter Human Use (21 C.F.R. § 347), which presently include: allantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category DI actives as defined by the U.S. Food and Drug Administration's Tentative Final Monograph on Skin Protectant Drug Products for Over-the-Counter Human Use (21 C.F.R. § 347), which presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, buffered mixture of cation and anion exchange resins, corn starch, trolamine, and the like. Further, other potential materials are Category II actives as defined by the U.S. Food and Drug Administration's Tentative Final Monograph on Skin Protectant Drug Products for Over-the-Counter Human Use (21 C.F.R. § 347), which include: bizmuth subnitrate, boric acid, ferric chloride, polyvinyl pyrrolidone vinyl acetate copolymers, sulfur, tannic acid, and the like. The skin care agent may be selected from these materials and mixtures thereof. As mentioned above, the materials for use should be safe.

The composition may include between about 0.001% and about 20% of the skin care agent. The concentration range of the skin care agents in the composition varies from material to material.

Hair Treatment Actives

Pyridinethione anti-dandruff particulates, especially 1-hydroxy-2-pyridinethione salts, are suitable particulate anti-dandruff agents. The concentration of pyridinethione anti-dandruff particulate typically ranges from about 0.01 wt. % to about 5 wt. %, based on the total weight of the composition, generally from about 0.1 wt. % to about 3 wt. t % Y, commonly from about 0.1 wt. % to about 2 wt. %. Suitable pyridinethione salts include those formed from heavy metals such as zinc, tin, cadmium, magnesium, aluminum and zirconium, generally zinc, typically the zinc salt of 1-hydroxy-2-pyridinethione (known as "zinc pyridinethione" or "ZPT"), commonly 1-hydroxy-2-pyridinethione salts in platelet particle form, wherein the particles have an average size of up to about 20 um, typically up to about 5 µm, commonly up to about 2.5 µm. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. As noted above, ZPT is a preferred pyridinethione salt.

In addition to the anti-dandruff active, compositions may also include one or more anti-fungal or anti-microbial actives in addition to the metal pyrithione salt actives. Suitable anti-microbial actives include coal tar, sulfur, charcoal, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Typical anti-microbials include itraconazole, ketoconazole, selenium sulphide and coal tar.

Under Arm Treatment Actives

The compositions of the present invention may comprise from about 0.1% to about 50% by weight of a solubilized antiperspirant active suitable for application to human skin. The concentration of antiperspirant active in the composition should be sufficient to provide the finished antiperspirant product with the desired perspiration wetness and odor control.

The compositions of the present invention preferably comprise, or provide finished product that comprises, solubilized antiperspirant active at concentrations of from about 0.1% to about 35%, preferably from about 3% to about 20%, even more preferably from about 4% to about 19%, by weight of the composition. All such weight percentages are calculated on an anhydrous metal salt basis exclusive of water and any complexing or buffering agent such as glycine, glycine salts, or other complexing or buffering agent.

The solubilized antiperspirant active for use in the compositions of the present invention include any compound, composition or other material having antiperspirant activity. Preferred antiperspirant actives include astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant compositions include those which conform to the formula:

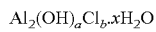

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4.

Preferred zirconium salts for use in the antiperspirant compositions include those which conform to the formula:

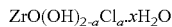

$$ZrO(OH)_{2-a}Cl_a \cdot xH_2O$$

wherein a is any number having a value of from about 0 to about 2; x is from about 1 to about 7; and wherein a and x may both have non-integer values. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas.

Aqueous Phase

The personal care rheological solid composition may include an aqueous carrier. The aqueous carrier which is used may be distilled, deionized, or tap water. Water may be present in any amount for the personal care rheological solid composition to be an aqueous solution. Water may be present in an amount of about 80 wt % to 99.5 wt %, alternatively about 90 wt % to about 99.5 wt %, alternatively about 92 wt % to about 99.5 wt %, alternatively about 95 wt %, by weight of the personal care rheological solid composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the personal care rheological solid composition for solubilizing perfumes or for stabilizing some preservatives, the level of monohydric alcohol may about 1 wt % to about 5 wt %, alternatively less than about 6 wt %, alternatively less than about 3 wt %, alternatively less than about 1 wt %, by weight of the personal care rheological solid composition.

However, other components can be optionally dissolved with the low molecular weight monohydric alcohols in the water to create an aqueous phase. Combined, these components are referred to as soluble active agents. Such soluble active agents include, but are not limited to, catalysts, activators, peroxides, enzymes, antimicrobial agents, preservatives, sodium chloride, surfactants, polyols, suncreens, probiotics, and vitamins. The crystallizing agent and insoluble active agents, including sunscreens, vitamins, probiotics, and emollients may be dispersed in the aqueous phase. The suspension agent may be dissolved in the aqueous phase (as with gums and other soluble polymers) or may be dispersed in the aqueous phase (as with clay particles).

Sensate

In embodiments, soluble active agent can include one or more components that provide a sensory benefit, often called a sensate. Sensates can have sensory attributes such as a warming, tingling, or cooling sensation. Suitable sensates include, for example, menthol, menthyl lactate, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, thymol, linalool, benzaldehyde, cinnamaldehyde glycerol acetal known as CGA. Winsense WS-5 supplied by Renessenz-Symrise, Vanillyl butyl ether known as VBE, and mixtures thereof.

In certain embodiments, the sensate comprises a coolant. The coolant can be any of a wide variety of materials. Included among such materials are carboxamides, menthol, ketals, diols, and mixtures thereof. Some examples of carboxamide coolants include, for example, paramenthan carboxyamide agents such as N-ethyl-p-menthan-3-carboxamide, known commercially as "WS-3", N,2,3-trimethyl-2-isopropylbutanamide, known as "WS-23," and N-(4-cyanomethylphenyl)-p-menthanecarboxamide, known as G-180 and supplied by Givaudan. G-180 generally comes as a 7.5% solution in a flavor oil, such as spearmint oil or peppermint oil. Examples of menthol coolants include, for example, menthol; 3-1-menthoxypropane-1,2-diol known as TK-10, manufactured by Takasago; menthone glycerol acetal known as MGA manufactured by Haarmann and Reimer; and menthyl lactate known as Frescolat® manufactured by Haarmann and Reimer. The terms menthol and menthyl as used herein include dextro- and levorotatory isomers of these compounds and racemic mixtures thereof.

In certain embodiments, the sensate comprises a coolant selected from the group consisting of menthol; 3-1-menthoxypropane-1,2-diol, menthyl lactate; N,2,3-trimethyl-2-isopropylbutanamide; N-ethyl-p-menthan-3-carboxamide; N-(4-cyanomethylphenyl)-p-menthanecarboxamide, and combinations thereof. In further embodiments, the sensate comprises menthol; N,2,3-trimethyl-2-isopropylbutanamide.

Surfactant

The personal care rheological solid compositions described herein can include one or more surfactants, which may be in a surfactant system. The one or more surfactants can be substantially free of sulfate-based surfactants. As can be appreciated, surfactants provide a cleaning benefit to soiled articles such as hair, skin, and hair follicles by facilitating the removal of oil and other soils. Surfactants generally facilitate such cleaning due to their amphiphilic nature which allows for the surfactants to break up, and form micelles around, oil and other soils which can then be rinsed out, thereby removing them from the soiled article. Suitable surfactants for a personal care rheological solid composition can include anionic moieties to allow for the formation of a coacervate with a cationic polymer. The surfactant can be selected from anionic surfactants, amphoteric surfactants, zwitterionic surfactants, non-ionic surfactants, and combinations thereof.

Personal care rheological solid compositions can employ sulfate-based surfactant systems (such as, but not limited to, sodium lauryl sulfate) because of their effectiveness in lather production, stability, clarity and cleansing. The personal care rheological solid compositions described herein are substantially free of sulfate-based surfactants. "Substantially free" of sulfate based surfactants as used herein means from about 0 wt % to about 3 wt %, alternatively from about 0 wt % to about 2 wt %, alternatively from about 0 wt % to about 1 wt %, alternatively from about 0 wt % to about 0.5 wt %, alternatively from about 0 wt % to about 0.25 wt %, alternatively from about 0 wt % to about 0.1 wt %, alternatively from about 0 wt % to about 0.05 wt %, alternatively from about 0 wt % to about 0.01 wt %, alternatively from about 0 wt % to about 0.001 wt %, and/or alternatively free of sulfates. As used herein, "free of" means 0 wt %.

Additionally, the surfactant systems described herein have from about 0 wt % to about 1 wt % of inorganic salts.

Suitable surfactants that are substantially free of sulfates can include sodium, ammonium or potassium salts of isethionates; sodium, ammonium or potassium salts of sulfonates; sodium, ammonium or potassium salts of ether sulfonates; sodium, ammonium or potassium salts of sulfosuccinates; sodium, ammonium or potassium salts of sulfoacetates; sodium, ammonium or potassium salts of glycinates; sodium, ammonium or potassium salts of sarcosinates; sodium, ammonium or potassium salts of glutamates; sodium, ammonium or potassium salts of alaninates; sodium, ammonium or potassium salts of carboxylates; sodium, ammonium or potassium salts of taurates; sodium, ammonium or potassium salts of phosphate esters; and combinations thereof.

The concentration of the surfactant in the composition should be sufficient to provide the desired cleaning and lather performance. The personal care rheological solid composition can comprise a total surfactant level of from about 6% to about 50%, from about 5% to about 35%, a total surfactant level of from about 10% to about 50%, by weight, from about 15% to about 45%, by weight, from about 20% to about 40%, by weight, from about 22% to about 35%, and/or from about 25% to about 30%.

The surfactant system can include one or more amino acid based anionic surfactants. Non-limiting examples of amino acid based anionic surfactants can include sodium, ammonium or potassium salts of acyl glycinates; sodium, ammonium or potassium salts of acyl sarcosinates; sodium, ammonium or potassium salts of acyl glutamates; sodium, ammonium or potassium salts of acyl alaninates and combinations thereof.

The amino acid based anionic surfactant can be a glutamate, for instance an acyl glutamate. The composition can comprise an acyl glutamate level from about 2% to about 22%, by weight, from about 3% to about 19%, by weight, 4% to about 17%, by weight, and/or from about 5% to about 15%, by weight.

Non-limiting examples of acyl glutamates can be selected from the group consisting of sodium cocoyl glutamate, disodium cocoyl glutamate, ammonium cocoyl glutamate, diammonium cocoyl glutamate, sodium lauroyl glutamate, disodium lauroyl glutamate, sodium cocoyl hydrolyzed wheat protein glutamate, disodium cocoyl hydrolyzed wheat protein glutamate, potassium cocoyl glutamate, dipotassium cocoyl glutamate, potassium lauroyl glutamate, dipotassium lauroyl glutamate, potassium cocoyl hydrolyzed wheat protein glutamate, dipotassium cocoyl hydrolyzed wheat protein glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallow glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallow glutamate, sodium cocoyl/palmoyl/sunfloweroyl glutamate, sodium hydrogenated tallowoyl Glutamate, sodium olivoyl glutamate, disodium olivoyl glutamate, sodium palmoyl glutamate, disodium palmoyl Glutamate, TEA-cocoyl glutamate, TEA-hydrogenated tallowoyl glutamate, TEA-lauroyl glutamate, and mixtures thereof.

The amino acid based anionic surfactant can be an alaninate, for instance an acyl alaninate. Non-limiting example of acyl alaninates can include sodium cocoyl alaninate, sodium lauroyl alaninate, sodium N-dodecanoyl-1-alaninate and combination thereof. The composition can comprise an acyl alaninate level from about 2% to about 20%, by weight, from about 7% to about 15%, by weight, and/or from about 8% to about 12%, by weight.

The amino acid based anionic surfactant can be a sarcosinate, for instance an acyl sarcosinate. Non-limiting examples of sarcosinates can be selected from the group consisting of sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroylglutamate/lauroylsarcosinate, disodium lauroamphodiacetate lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and combinations thereof.

The amino acid based anionic surfactant can be a glycinate for instance an acyl glycinate. Non-limiting example of acyl glycinates can include sodium cocoyl glycinate, sodium lauroyl glycinate and combination thereof.

The composition can contain additional anionic surfactants selected from the group consisting of sulfosuccinates, isethionates, sulfonates, sulfoacetates, glucose carboxylates, alkyl ether carboxylates, acyl taurates, and mixture thereof.

Non-limiting examples of sulfosuccinate surfactants can include disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and combinations thereof. The composition can comprise a sulfosuccinate level from about 2% to about 22%, by weight, from about 3% to about 19%, by weight, 4% to about 17%, by weight, and/or from about 5% to about 15%, by weight.

Suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride. Non-limiting examples of isethionates can be selected from the group consisting of sodium lauroyl methyl isethionate, sodium cocoyl isethionate, ammonium cocoyl isethionate, sodium hydrogenated cocoyl methyl isethionate, sodium lauroyl isethionate, sodium cocoyl methyl isethionate, sodium myristoyl isethionate, sodium oleoyl isethionate, sodium oleyl methyl isethionate, sodium palm kerneloyl isethionate, sodium stearoyl methyl isethionate, and mixtures thereof.

Non-limiting examples of sulfonates can include alpha olefin sulfonates, linear alkylbenzene sulfonates, sodium laurylglucosides hydroxypropylsulfonate and combination thereof.

Non-limiting examples of sulfoacetates can include sodium lauryl sulfoacetate, ammonium lauryl sulfoacetate and combination thereof.

Non-limiting example of glucose carboxylates can include sodium lauryl glucoside carboxylate, sodium cocoyl glucoside carboxylate and combinations thereof.

Non-limiting example of alkyl ether carboxylate can include sodium laureth-4 carboxylate, laureth-5 carboxylate, laureth-13 carboxylate, sodium C12-13 pareth-8 carboxylate, sodium C12-15 pareth-8 carboxylate and combination thereof.

Non-limiting example of acyl taurates can include sodium methyl cocoyl taurate, sodium methyl lauroyl taurate, sodium methyl oleoyl taurate and combination thereof.

The surfactant system may further comprise one or more amphoteric surfactants and the amphoteric surfactant can be selected from the group consisting of betaines, sultaines, hydroxysultanes, amphohydroxypropyl sulfonates, alkyl amphoactates, alkyl amphodiacetates and combination thereof.

Examples of betaine amphoteric surfactants can include coco dimethyl carboxymethyl betaine, cocoamidopropyl betaine (CAPB), cocobetaine, lauryl amidopropyl betaine (LAPB), oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines can include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

Non-limiting example of alkylamphoacetates can include sodium cocoyl amphoacetate, sodium lauroyl amphoacetate and combination thereof.

The amphoteric surfactant can comprise cocamidopropyl betaine (CAPB), lauramidopropyl betaine (LAPB), and combinations thereof.

The personal care rheological solid composition can comprise an amphoteric surfactant level from about 0.5 wt % to about 20 wt %, from about 1 wt % to about 15 wt %, from about 2 wt % to about 13 wt %, from about 3 wt % to about 15 wt %, and/or from about 5 wt % to about 10 wt %.

The surfactant system can have a weight ratio of anionic surfactant to amphoteric surfactant from about 1:5 to about 10:1, from about 1:2 to about 7:1, from 1:1 to about 5:1, and/or from about 2:1 to about 4:1. The surfactant system can have a weight ratio of anionic surfactant to amphoteric surfactant greater than 1:1, greater than 3:2, greater than 9:5, and/or greater than 2:1.

The surfactant system may further comprise one or more non-ionic surfactants and the non-ionic surfactant can be selected from the group consisting alkyl polyglucoside, alkyl glycoside, acyl glucamide and mixture thereof. Non-limiting examples of alkyl glucosides can include decyl glucoside, cocoyl glucoside, lauroyl glucoside and combination thereof.

Non-limiting examples of acyl glucamide can include lauroyl/myristoyl methyl glucamide, capryloyl/caproyl methyl glucamide, lauroyl/myristoyl methyl glucamide, cocoyl methyl glucamide and combinations thereof.

Antimicrobial Compounds

In embodiments, soluble active agent can include an effective amount of one or more antimicrobials for reducing the number of viable microbes. For example, antimicrobials may include, without being limited to, piroctone olamine, hexamidine, magnesium carbonate, zinc carbonate, thymol, magnesium hydroxide, dead sea salt, magnesium hydroxide and magnesium carbonate hydroxide, partially carbonated magnesium hydroxide, calcium carbonate, polyvinyl formate, salycilic acid, niacinamide, phenoxyethanol, eugenol, linolenic acid, dimethyl succinate, citral, triethyl citrate, sepiwhite, baking soda, partially carbonated magnesium hydroxide, magnesium carbonate hydroxide, cinnamon essential oil, cinnamon bark essential oil, cinnamic aldehyde, and combinations thereof.

In general, the total amount of antimicrobial used in the present invention may be from about 0.1% to about 30%, by weight, of the personal care rheological solid composition. Some antimicrobials may be used in amounts as low as about 0.1%, by weight of the personal care rheological solid composition, such as if using piroctone olamine or hexamidine as the primary antimicrobial, while others could be as high as about 25%, such as if using magnesium hydroxide or magnesium hydroxide and magnesium carbonate hydroxide as the primary antimicrobial (primary antimicrobial being the antimicrobial present in the composition in the highest amount). In the latter cases, baking soda might still be used at a lower level, such as from about 0.1% to about 6%, as a secondary antimicrobial, or not at all.

Preservatives

In embodiments, soluble active agent can include a preservative. The preservative may be present in an amount sufficient to prevent spoilage or prevent growth of inadvertently added microorganisms for a specific period of time, but not sufficient enough to contribute to the odor neutralizing performance of the personal care rheological solid composition. In other words, the preservative is not being used as the antimicrobial compound to kill microorganisms on the surface onto which the personal care rheological solid composition is deposited in order to eliminate odors produced by microorganisms. Instead, it is being used to prevent spoilage of the personal care rheological solid composition in order to increase the shelf-life of the personal care rheological solid composition.

The preservative can be any organic preservative material. Suitable water-soluble preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Huls America; formaldehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation; 1,2-Benzisothiazolin-3-one; Acticide MBS.

Suitable levels of preservative are from about 0.0001 wt. % to about 0.5 wt. %, alternatively from about 0.0002 wt. % to about 0.2 wt. %, alternatively from about 0.0003 wt. % to about 0.1 wt. %, by weight of the personal care rheological solid composition.

Adjuvants

Adjuvants can be added to the personal care rheological solid composition herein for their known purposes. Such adjuvants include, but are not limited to, water soluble metallic salts, including zinc salts, copper salts, and mixtures thereof; colorants; antioxidants; aromatherapy agents and mixtures thereof.

The compositions of the present invention can also comprise any additive usually used in the field under consideration. For example, non-encapsulated pigments, film forming agents, dispersants, antioxidants, essential oils, preserving agents, fragrances, liposoluble polymers that are dispersible in the medium, fillers, neutralizing agents, silicone elastomers, cosmetic and dermatological oil-soluble active agents such as, for example, emollients, moisturizers, vitamins, anti-wrinkle agents, essential fatty acids, sunscreens, and mixtures thereof can be added.

Solvents

The composition can contain a solvent. Non-limiting examples of solvents can include ethanol, glycerol, propylene glycol, polyethylene glycol 400, polyethylene glycol 200, and mixtures thereof. In one example the composition comprises from about 0.5% to about 15% solvent, in another example from about 1.0% to about 10% solvent, and in another example from about 1.0% to about 8.0% solvent, and in another example from about 1% solvent to about 5% solvent.

Vitamins

As used herein. "xanthine compound" means one or more xanthines, derivatives thereof, and mixtures thereof. Xanthine Compounds that can be useful herein include, but are not limited to, caffeine, xanthine, 1-methyl xanthine, theophylline, theobromine, derivatives thereof, and mixtures thereof. Among these compounds, caffeine is preferred in view of its solubility in the composition. The composition can contain from about 0.05%, preferably from about 2.0%, more preferably from about 0.1%, still more preferably from about 1.0%, and to about 0.2%, preferably to about 1.0%, more preferably to about 0.3% by weight of a xanthine compound As used herein, "vitamin B3 compound" means a one or more compounds having the formula:

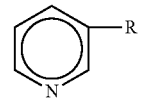

wherein R is —CONH$_2$ (i.e., niacinamide). —COOH (i.e., nicotinic acid) or —CH$_2$OH (i.e., nicotinyl alcohol); derivatives thereof; mixtures thereof; and salts of any of the foregoing.

Exemplary derivatives of the foregoing vitamin B3 compounds include nicotinic acid esters, including non-vasodilating esters of nicotinic acid (e.g. tocopherol nicotinate, and myristyl nicotinate), nicotinyl amino acids, nicotinyl alcohol esters of carboxylic acids, nicotinic acid N-oxide and niacinamide N-oxide. The composition can contain from about 0.05%, preferably from about 2.0%, more preferably from about 0.1%, still more preferably from about 1.0%, and to about 0.1%, preferably to about 0.5%, more preferably to about 0.3% by weight of a vitamin B3 compound As used herein, the term "panthenol compound" is broad enough to include panthenol, one or more pantothenic acid derivatives, and mixtures thereof, panthenol and its derivatives can include D-panthenol ([R]-2,4-dihydroxy-N-[3-hydroxypropyl)]-3,3-dimethylbutamide), DL-panthenol, pantothenic acids and their salts, preferably the calcium salt, panthenyl triacetate, royal jelly, panthetine, pantotheine, panthenyl ethyl ether, pangamic acid, pantoyl lactose, vitamin B complex, or mixtures thereof. The composition can contain from about 0.01%, preferably from about 0.02%, more preferably from about 0.05%, and to about 3%, preferably to about 1%, more preferably to about 0.5% by weight of a panthenol compound Sodium chloride (and other sodium salts) is a particular useful additive to the aqueous phase to adjust the thermal stability of compositions, but must be added into the composition with particular care (Example 3). Not wishing to be bound by theory, sodium chloride is thought to 'salt out' inventive crystallizing agents decreasing their solubility. This has the effect of increasing the thermal stability temperature of the personal care rheological solid composition as measured by the THERMAL STABILITY TEST METHOD. For example, Optimal Chain Length crystallizing agents can have the thermal stability temperatures increased as much as 15° C. with sodium chloride addition. This is particularly valuable as the addition of other ingredients into the aqueous phase often lower the thermal stability temperature in the absence of sodium chloride. Surprisingly, adding sodium chloride can lead to adverse effects in the preparation of the personal care rheological solid compositions. It is preferable in most making processes, to add sodium chloride into the hot crystallizing agent aqueous phase before cooling to form the mesh. However, adding too much may cause 'curding' of the crystallizing agents and undesirable compositions. The sodium chloride may also be added after the formation of the mesh, to provide the benefit of raising the thermal stability temperature at higher levels without curding. Finally, while the thermal stability temperature is increased with addition of sodium chloride, the addition of other non-sodium salts changes the fibrous nature of the crystals formed from the crystallizing agents, to form plates or platelet crystals, which are not rheological solids.

Personal Care Rheological Solid Composition Properties

Phase Stability

Phase stability, as used herein, is a measure the effectiveness of the suspension agent(s) to prevent the sedimentation or creaming of dispersed active particles through a viable process, is necessary. A hot mixture of solubilized crystallizing agent in water at processing temperatures has a viscosity on the order of several milli-pascal seconds. At this stage, actives are added and dispersed as particles in the mixture. The active particles tend to cream (i.e. rise) or sediment (i.e. settle) in the time before crystallization of the crystallizing agent, leading to consumer-unacceptable separation of the materials. The suspension agent(s) prevent bulk separation of dispersed active particles during crystallization and allows a mesh of fiber-like crystal particles to entrain the dispersed active particles. Not wishing to be bound by theory, it is believed that the suspension agent(s) either increases the suspension viscosity or enables a yield stress to the mixture that prevents active particle separation. A value of '0' is not preferred, a value of '1' is preferred values, and a value of '2' is most preferred are, as determined using the PHASE STABILITY TEST METHOD, as described below.

Stability Temperature

Stability temperature, as used herein, is the temperature at which most or all of the crystallizing agent completely dissolves into an aqueous phase, such that a composition no longer exhibits a stable solid structure and may be considered a liquid. In embodiments of the present invention the stability temperature range may be from about 40° C. to about 95° C., about 40° C. to about 90° C., about 50° C. to about 80° C., or from about 60° C. to about 70° C., as these temperatures are typical in a supply chain. Stability temperature can be determined using the THERMAL STABILITY TEST METHOD, as described below.

Firmness

Depending on the intended application, such as a stick, firmness of the composition may also be considered. The firmness of a composition may, for example, be expressed in Newtons of force. For example, compositions of the present invention comprising 1-3 wt % crystallizing agent may give values of about 4-about 12 N, in the form of a solid stick or coating on a sheet. As is evident, the firmness of the composition according to embodiments of the present invention may, for example, be such that the composition is advantageously self-supporting and can release liquids and/or actives upon application of low to moderate force, for example upon contact with a surface, to form a satisfactory deposit on a surface, such as the skin and/or superficial body growths, such as keratinous fibers. In addition, this hardness may impart good impact strength to the inventive compositions, which may be molded or cast, for example, into stick or sheet form, such as a wipe product. The composition of the invention may also be transparent or clear, including for example, a composition without pigments. Preferred firmness is between about 0.1 N to about 50.0 N, more preferably between about 0.5 N to about 40.0 N, more preferably between about 1.0 N to about 30.0 N and most preferably between about 2.5 N to about 15.0 N. The firmness may be measured using the FIRMNESS TEST METHOD, as described below.

Aqueous Phase Expression

Depending on the intended application, such as a stick, aqueous phase expression of the composition may also be considered. This is a measure of the amount of work need per unit volume to express the aqueous phase from the compositions, with larger values meaning it becomes more difficult to express liquid. A low value might be preferred, for example, when applying the composition to the skin. A high value might be preferred, for example, when the composition is applied to a substrate that requires 'dry-to-the-touch-but-wet-to-the-wipe' properties. Preferred values are between about 100 J m−3 to about 8,000 J m−3, more preferably between about 1,000 J m−3 to about 7,000 J m−3, and most preferably between about 2,000 J m−3 to about 5,000 J m−3. The liquid expression may be measured using the AQUEOUS PHASE EXPRESSION TEST METHOD, as described herein.

Firmness Test Method

All samples and procedures are maintained at room temperature (25 t 3° C.) prior to and during testing, with care to ensure little or no water loss.

All measurements were made with a TA-XT2 Texture Analyzer (Texture Technology Corporation, Scarsdale, N.Y., U.S.A.) outfitted with a standard 45° angle penetration cone tool (Texture Technology Corp., as part number TA-15).

To operate the TA-XT2 Texture Analyzer, the tool is attached to the probe carrier arm and cleaned with a low-lint wipe. The sample is positioned and held firmly such that the tool will contact a representative region of the sample. The tool is reset to be about 1 cm above the product sample.

The sample is re-position so that the tool will contact a second representative region of the sample. A run is done by moving the tool at a rate of 2 mm/second exactly 10 mm into the sample. The "RUN" button on the Texture Analyzer can be pressed to perform the measurement. A second run is done with the same procedure at another representative region of the sample at sufficient distance from previous measurements that they do not affect the second run. A third run is done with the same procedure at another representative region of the sample at sufficient distance from previous measurements that they do not affect the third run.

The results of the FIRMNESS TEST METHOD, are all entered in the examples in the row entitles 'Firmness'. In general, the numeric value is returned as the average of the maximum value of three measurements as described above, except in one of the two cases:

1) the composition does not form a homogenous rheological solid (e.g. completely or partially liquid), the value of 'NM1' is returned;

2) and, the composition curds during making, the value of 'NM2' is returned.

Thermal Stability Test Method

All samples and procedures are maintained at room temperature (25 t 3° C.) prior to testing.

Sampling is done at a representative region on the sample, in two steps. First, a spatula is cleaned with a laboratory wipe and a small amount of the sample is removed and discarded from the top of the sample at the region, to create a small square hole about 5 mm deep. Second, the spatula is cleaned again with a clean laboratory wipe, and a small amount of sample is collected from the square hole and loaded into DSC pan.

The sample is loaded into a DSC pan. All measurements are done in a high-volume-stainless-steel pan set (TA part #900825.902). The pan, lid and gasket are weighed and tared on a Mettler Toledo MT5 analytical microbalance (or equivalent; Mettler Toledo, LLC., Columbus, Ohio). The sample is loaded into the pan with a target weight of 20 mg (+/−10 mg) in accordance with manufacturer's specifications, taking care to ensure that the sample is in contact with the bottom of the pan. The pan is then sealed with a TA High Volume Die Set (TA part #901608.905). The final assembly is measured to obtain the sample weight.

The sample is loaded into TA Q Series DSC (TA Instruments, New Castle, Del.) in accordance with the manufacture instructions. The DSC procedure uses the following settings: 1) equilibrate at 25° C.; 2) mark end of cycle 1; 3) ramp 1.00° C./min to 90.00° C.; 4) mark end of cycle 3; then 5) end of method; Hit run.

The results of the TEMPERATURE STABILITY TEST METHOD, are all entered in the examples in the row entitles 'Temperature'. In general, the numeric value is returned as described above, except in one of the two cases:

1) the composition does not form a homogenous rheological solid (e.g. completely or partially liquid) and is not suitable for the measurement, the value of 'NM3' is returned;

2) and, the composition curds during making and is not suitable for the measurement, the value of 'NM4' is returned.

Aqueous Phase Expression Test Method

All samples and procedures are maintained at room temperature 25 (t 3° C.) prior to testing.

Measurements for the determination of aqueous phase expression were made with a TA Discovery HR-2 Hybrid Rheometer (TA Instruments, New Castle, Del.) and accompanying TRIOS software version 3.2.0.3877, or equivalent. The instrument is outfitted with a DHR Immobilization Cell (TA Instrument) and 50 mm flat steel plate (TA Instruments). The calibration is done in accordance with manufacturer's recommendations, with special attention to measuring the bottom of the DHR Immobilization Cell, to ensure this is established as gap=0.

Samples are prepared in accordance with EXAMPLE procedures. It is critical that the sample be prepared in Speed Mixer containers (Flak-Tech, Max 60 Cup Translucent, Cat #501 222t), so that the diameter of the sample matches the diameter of the HR-2 Immobilization Cell. The sample is released from the containers by running a thin spatula between the edge of the container and the sample. The container is gently turned over and placed on a flat surface. A gentle force is applied to the center of the bottom of the overturned container, until the sample releases and gently glides out of the container.

The sample is carefully placed in the center ring of the DHR Immobilization Cell. Care is used to ensure that the sample is not deformed and re-shaped through this entire process. The diameter of the sample should be slightly smaller than the inner diameter of the ring. This ensures that force applied to the sample in latter steps does not significantly deform the cylindrical shape of the sample, instead allowing the aqueous phase to escape through the bottom of the sample. This also ensures that any change in the height of the sample for the experiment is equivalent to the amount of aqueous phase expressed during the test. At the end of the measurement, one should confirm that the aqueous phase is indeed expressed from the sample through the measurement, by looking for aqueous phase in the effluent tube connected to the Immobilization Cell. If no aqueous phase is observed, the sample is deemed not to express aqueous phase and is not inventive.

Set the instrument settings as follows. Select Axial Test Geometry. Then, set "Geometry" options: Diameter=50 mm; Gap=45000 um; Loading Gap=45000 um; Trim Gap Offset=50 um; Material='Steel'; Environmental System="Peltier Plate". Set "Procedure" options: Temperature=25° C.; Soak Time=0 sec; Duration=2000 sec; Motor Direction="Compression"; Constant Linear Rate=2 um sec−1; Maximum Gap Change=0 um; Torque=0 uN-m; Data Acquisition='save image' every 5 sec.

Manually move the steel tool within about 1000 um of the surface of the sample, taking care that the tool does not touch the surface. In the "Geometry" options, reset Gap to this distance.

Start the run.

The data is expressed in two plots:

1) Plot 1: Axial Force (N) on the left-y-axis and Step Time (s) on the x-axis;

2) Plot 2: Gap (um) on the right-y-axis and Step Time (s) on the x-axis.

The Contact Time—T(contact), is obtained from Plot 1. The T(contact) is defined as the time when the tool touches the top of the sample. The T(contact) is the Step Time when the first Axial Force data point exceeds 0.05 N.

The Sample Thickness—L, is the gap distance at the Contact Time, and expressed in units of meters.

The Time of Compression—T(compression), is the Step Time at which the gap is 0.85*L, or 15% of the sample.

The Work required to squeeze the aqueous phase from the structure is the area under the Axial Force curve in Plot 1 between T(contact) and T(compression) multiplied by Constant Linear Rate, or 2e−6 m s−1 normalized by dividing the total volume of expressed fluids, and is expressed in units of Joules per cubic meter (J m−3).

The results of the AQUEOUS PHASE EXPRESSION TEST METHOD, are all entered in the examples in the row entitled 'AP Expression'. In general, the numeric value, as the average of at least two values is returned as described, except in one of the three cases:

1) the composition does not form a homogenous rheological solid (e.g. completely or partially liquid) and is not suitable for the measurement, the value of 'NM5' is returned;

2) the composition curds during making and is not suitable for the measurement, the value of 'NM6' is returned;

3) the composition is a rheological solid but too soft to effectively load in the device, the value of 'NM7' is returned;

4) and the composition is too hard so that the force exceeds 50 N before the 15% compression, the value of 'NM8' is returned;

Blend Test Method

All samples and procedures are maintained at room temperature 25 (t 3° C.) prior to testing.

Samples are prepared by weighing 4 mg (+/−1 mg) of a 3% fatty acid in water solution into a scintillation vial with a PTFE septum and then adding 2 mL of ethanol ACS grade or equivalent. A cap is then placed on the vial and the sample is mixed until the sample is homogenous. The vial is then placed in a 70° C. oven with the cap removed to evaporate the ethanol (and water), after which it is allowed to cool to room temperature.

A pipettor is used to dispense 2 mL of BF3-methanol (10% Boron Trifluoride in methanol, Sigma Aldrich #15716) into the vial, and the capped tightly. The sample is placed on a VWR hot plate set at 70° C. until the sample is homogenous, and then for an additional 5 min before cooling to room temperature.

A saturated sodium chloride solution is prepared by adding sodium chloride salt ACS grade or equivalent to 10 mL of distilled water at ambient temperature. Once the vial is at room temperature, 4 mL of the saturated sodium chloride solution are added to the vial and swirled to mix. Then, 4 mL of hexane, ACS grade or equivalent, are added to the vial which is then capped and shaken vigorously. The sample is then placed on a stationary lab bench and until the hexane and water separate into two phases.

A transfer pipet is used to transfer the hexane layer into a new 8 mL vial, and then 0.5 g of sodium sulfate, ACS grade or equivalent, is added to dry the hexane layer. The dried hexane layer is then transferred to a 1.8 mL GC vial for analysis.

Samples are analyzed using an Agilent 7890B (Agilent Technologies Inc., Santa Carla, Calif.), or equivalent gas chromatograph, equipped with capillary inlet system and flame ionization detector with peak integration capabilities, and an Agilent DB-FastFAME (#G3903-63011), or equivalent column.

The gas chromatograph conditions and settings are defined as follows: uses Helium UHP grade, or regular grade helium purified through gas purification system, as a carrier gas, and is set at a constant flow mode of 1.2 mL/minute (velocity of 31.8 cm/sec); has an oven temperature program that is set for 100° C. for 2 minutes, and increased at a rate of 10° C. per minute until it reaches 250 C for 3 minutes; the injector temperature is set to 250° C. and the detector temperature is set to 280° C.; the gas flows are set to 40 mL/minute for hydrogen, 400 mL/minute for air, and 25 mL/minute for the Make-up (helium); and the injection volume and split ratio is defined a 1 uL, split 1:100 injection.

The instrument is calibrated using a 37-Component FAME standard mixture (Supelco #CRM47885), or equivalent calibration standard. The Response Factor and Normalized Response Factor based on n-C16 FAME standard.

Response Factor is calculated for each component by dividing the FAME FID Area account of an analyte in the calibration solution by the concentration of the identical FAME analyte in the calibration solution.

The Normalized Response Factor is calculated by dividing the Response Factor of each component by the Response Factor of n-C16 methyl ester that has been defined as 1.00.

The Normalized FAME FID Area is calculated with the Normalized Response Factor by dividing the FAME FID area (component) by the Normalized Response Factor (component).

The FAME weight percent of each component is calculated by dividing the Normalized FAME FID area (component) by the Normalized FAME FID area (total of each component) and then multiplying by one hundred.

The Conversion Factor from FAME to free Fatty Acid is calculated by dividing the Molecular Weight of the Target Fatty Acid by the Molecular Weight of the Target FAME.

The Normalized Fatty Acid FID Area is calculated by multiplying the Normalized FAME FID Area by the Conversion Factor from FAME to free Fatty Acid.

The Fatty Acid Weight Percent of each component is calculated by dividing the Normalized Fatty Acid FID Area (component) by the Normalized FA FID Area (total of each component) and the multiplying the result by one hundred.

The Conversion Factor from FAME to free Fatty Acid Sodium Salt is calculated by dividing the Molecular Weight of the Target Fatty Acid Sodium Salt by the molecular weight of the Target FAME.

The Normalized Fatty Acid Sodium Salt FID Area is calculated by multiplying the Normalized FAME FID Area by the Conversion Factor from FAME to free Fatty Acid Sodium Salt.

The Weight percent of each Fatty Acid Sodium Salt component was calculated by dividing the normalized Fatty Acid Sodium Salt FID area (component) by the Normalized Fatty Acid Sodium Salt FID area (total of each component) and then multiplying by one hundred.

Purity of the crystallizing agent is described in the following ways:

Optimal Purity—Po, which is the mass fraction of the optimal chain length molecules in the crystallizing agent blend calculated as:

$$Po = \frac{\Sigma Mo}{Mt}$$

where Mo is the mass of each optimal chain length in the crystallizing agent and Mt is the total mass of the crystallizing agent.

Single Purity—Ps, which is the mass fraction of the most common chain length in the crystallizing agent blend calculated as:

$$Ps = \frac{Ms}{Mt}$$

where Ms is the mass of the most common chain length in the crystallizing agent and Mt is the total mass of the crystallizing agent. The value is expressed in brackets—[Ms], if the most common chain length is selected from the group of unsuitable chain length molecules.

Phase Stability Test Method

Samples are prepared in accordance with EXAMPLE procedures.

Each of the samples is visually inspected for phase stability and graded based on the follow:

(most preferred) A grade of "2" is given if the composition appeared stable with no discernable separation of the beads (i.e. uniform);

(preferred) A grade of "1" is given if the preparation appeared with no more than 25% by number of the tracer beads on the top or bottom of the composition;

(not preferred) A grade of "0" is given if the composition appeared unstable as evident by nearly complete separation of the beads with more than 75% by number on the top and bottom of the composition.

For examples that do not contain beads the entire sample is placed into a container (Flak-Tech, Max 60 Cup Translucent, Cat #501 222t) and placed in an oven (Yamato, DKN 400; Yamato Scientific Co., Ltd., Tokyo, Japan, or equivalent) set to 60° C. for one hour. The containers are placed on a bench top at room temperature (25 t 3° C. 'Separation' in the samples describes the creaming and/or sedimentation of the insoluble active particles.

Each of the samples is visually inspected for phase stability and graded based on the follow:
- (most preferred) A grade of "2" is given if the composition appeared stable with no discernable or visual separation of the insoluble active particles;
- (preferred) A grade of "1" is given if the preparation appeared with only a few drops (estimated less than 25 wt % of the total amount of added insoluble active agent) on the top and/or bottom of the composition. In some compositions, this may result in a 'slick' appearance on the surface;
- (not preferred) A grade of "0" is given if the compositions appeared unstable as evident by nearly complete separation of the insoluble active agent on the top or the bottom of the composition (estimated less than 75 wt % of the total amount of added insoluble active agent). In the case of oils, the amounts are sufficient to have the oil visually flow when the sample is turned sideways.

EXAMPLES

Materials List
(1) Water: Millipore, Burlington, Mass. (18 m-ohm resistance)
(2) Sodium caprate (sodium decanoate, NaC10): TCI Chemicals, Cat # D0024
(3) Sodium laurate (sodium dodecanoate, NaC12): TCI Chemicals, Cat # D0024
(4) Sodium myristate (sodium tetradecanoate, NaC14): TCI Chemicals, Cat. # M0483
(5) Sodium palmitate (sodium hexadecanoate, NaC16): TCI Chemicals, Cat. # P0007
(6) Sodium stearate (sodium octadecanoate, NaC18): TCI Chemicals, Cat. # S0081
(7) Sodium oleate (sodium trans-9-octadecanoate, NaC18:1): TCI Chemicals, Cat #00057
(8) Pentadecylic acid (pentadecanoic acid, HC15): TCI Chemicals, Cat # P0035
(9) Margaric acid (heptadecanoic acid, HC17): TCI Chemicals, Cat # H0019
(10) Nonadecylic acid (nonadecanoic acid, HC19): TCI Chemicals, Cat # N0283
(11) C1270 K ID: P&G Chemicals, Cincinnati, Ohio) prod. code 10275803
(12) C1618 K ID: P&G Chemicals, Cincinnati, Ohio) prod. code 10275805
(13) C1218 K ID: P&G Chemicals, Cincinnati, Ohio) prod. code 10275798
(14) C1214 K ID: P&G Chemicals, Cincinnati, Ohio) prod. code 10275796
(15) NaOH: 0.10 M, Fluka Chemical, Cat #319481-500ML
(16) Sodium chloride (NaCl): VWR, Cat # BDH9286-500G
(17) Lauric acid (HL): TCI Chemicals, Cat # L0011
(18) NaOH: 1.0 N, Honeywell/Fluka, Cat #35256-1L Example 1

These include samples containing crystallizing agents with a Po value of about 1 and Ps value of also about 1, as determined by the BLEND TEST METHOD, contrasting optimal and unsuitable crystallizing agents. Examples A-E (TABLEs 1-2) show samples prepared with different weight percentage of sodium tetradecanoate. The increasing concentrations increase both firmness and temperature stability of the samples, but also make it more difficult to express aqueous phase, as reflected in the aqueous phase expression value. As Example E shows—at about 9 wt %, it is no longer practical to express aqueous phase, as has been observed with soap bars that use these materials as gelling agents. Examples F-G (TABLE 2), show that other optimal chain length crystallizing agents, share similar trends as the previous examples. Example I-K (TABLE 3) have unsuitable crystallizing agents, and the sample compositions result in liquids. Not wishing to be bound by theory, it is believed these crystallizing agents are either too soluble (e.g. low Krafft Temperature) or 'kinks' from unsaturation in the chains disrupts crystallization. Examples L-M (TABLE 4) demonstrate that it is possible to create compositions with odd-chain length crystallizing agents. It is believed odd-chain-length crystallizing agents crystallize in a different manner than even chain-length crystallizing agents, so that it is surprising these compositions still form effective mesh structures.

Preparation of Compositions

Compositions were prepared using a heated mixing device. An overhead mixer (IKA Works Inc, Wilmington, N.C., model RW20 DMZ) and a three-blade impeller design was assembled. All preparations were heated on a heating-pad assembly (VWR, Radnor, Pa., 7×7 CER Hotplate, cat. no. NO97042-690) where heating was controlled with an accompanying probe. All preparations were done in a 250 ml stainless steel beaker (Thermo Fischer Scientific, Waltham, Mass.).

Samples A-K were prepared by first adding Water (1; the number references the component's listing on the Material List) and crystallizing agent (2-7) to the beaker. The beaker was placed on the heating-pad assembly. The overhead stirrer was placed in the beaker and set to rotate at 100 rpm. The heater was set at 80° C. The preparation was heated to 70° C. The solution was then divided into three 60 g plastic jars (Flak-Tech, Max 60 Cup Translucent, Cat #501 222t): one jar was filled to 50 ml and two jars filled to 25 ml (Samples A-G). The samples were cooled at room temperature 25 (t 3° C.) until solid. Firmness measurements were made on the 50 ml sample with the FIRMNESS TEST METHOD and a thermal stability measurement was made by the THERMAL STABILITY TEST METHOD on the 50 ml sample. Water-expression measurements were made by the AQUEOUS PHASE EXPRESSION TEST METHOD on the two 25 ml samples. Representative data demonstrates that the prototypes exhibit the required properties for these personal care rheological solid compositions.

Samples L-M were prepared by first adding NaOH (15) and fatty acid (8-10) to the beaker. The amount of NaOH was determined by acid number (AOCS Official Method Db 3-48—Free Acids or Free Alkali in Soap and Soap Products). The beaker was placed on the heating-pad assembly. The overhead stirrer was placed in the beaker and set to rotate at 100 rpm. The heater was set at 80° C. The preparation was heated to 70° C. The solution was then divided into three 60 g plastic jars (Flak-Tech, Max 60 Cup Translucent, Cat #501 222t): one jar was filled to 50 ml and two jars filled to 25 ml. The samples were cooled at room temperature 25 (t 3° C.) until solid. Firmness measurements were made on the 50 ml sample with the FIRMNESS TEST METHOD and a thermal stability measurement was made by the THERMAL STABILITY TEST METHOD on the 50 ml sample. Water-expression measurements were made by the AQUEOUS PHASE EXPRESSION TEST METHOD on the two 25 ml samples and blend was determined from the BLEND TEST METHOD. Representative data demonstrates that the prototypes exhibit the required properties of firmness, aqueous phase expression and thermal stability for these personal care rheological solid compositions.

TABLE 1

|  | Sample A Inventive | Sample B Inventive | Sample C Inventive | Sample D Inventive |
|---|---|---|---|---|
| (1) Water | 99.501 g | 99.001 g | 97.001 g | 95.001 g |
| (2) NaC10 | — | — | — | — |
| (3) NaC12 | — | — | — | — |
| (4) NaC14 | 0.500 g | 1.003 g | 3.001 g | 5.003 g |
| (5) NaC16 | — | — | — | — |
| (6) NaC18 | — | — | — | — |
| (7) NaC18:1 | — | — | — | — |
| % Crystallizing Agent | 0.5 wt % | 1.0 wt % | 3.0 wt % | 5.0 wt % |
| Firmness | 0.51N | 1.24N | 8.65N | 14.31N |
| AP Expression | NM7 | 340 J m-3 | 6,260 J m-3 | 7,730 J m-3 |
| Temperature | 46.7° C. | 45.0° C. | 48.5° C. | 54.3° C. |
| Po | 1.00 | 1.00 | 1.00 | 1.00 |
| Ps | 1.00 | 1.00 | 1.00 | 1.00 |

TABLE 2

|  | Sample E Comparative | Sample F Inventive | Sample G Inventive |
|---|---|---|---|
| (1) Water | 91.000 g | 99.501 g | 93.002 g |
| (2) NaC10 | — | — | — |
| (3) NaC12 | — | — | — |
| (4) NaC14 | 9.000 g | — | — |
| (5) NaC16 | — | 0.500 g | 7.002 g |
| (6) NaC18 | — | — | — |
| (7) NaC18:1 | — | — | — |
| % Crystallizing Agent | 9.0 wt % | 0.5 wt % | 7.0 wt % |
| Firmness | 40.92N | 0.51N | 5.03N |
| AP Expression | NM8 | NM7 | 2,550 J m-3 |
| Temperature | 56.4° C. | 59.0° C. | 64.3° C. |
| Po | 1.00 | 1.00 | 1.00 |
| Ps | 1.00 | 1.00 | 1.00 |

TABLE 3

|  | Sample I Comparative | Sample J Comparative | Sample K Comparative |
|---|---|---|---|
| (1) Water | 48.500 g | 48.611 g | 48.740 g |
| (2) NaC10 | 1.500 g | — | — |
| (3) NaC12 | — | 1.547 g | — |
| (4) NaC14 | — | — | — |
| (5) NaC16 | — | — | — |
| (6) NaC18 | — | — | — |
| (7) NaC18:1 | — | — | 1.505 g |
| % Crystallizing Agent | 3.0 wt % | 3.1 wt % | 3.0 wt % |
| Firmness | NM1 | NM1 | NM1 |
| AP Expression | NM5 | NM5 | NM5 |
| Temperature | NM3 | NM3 | NM3 |
| Po | 0.00 | 0.00 | 0.00 |
| Ps | [1.00] | [1.00] | [1.00] |

TABLE 4

|  | Sample L Inventive | Sample M Inventive |
|---|---|---|
| (8) H C15 | — | 2.561 g |
| (9) H C17 | 2.761 g | — |
| % Crystallizing Agent | 2.76 wt % | 2.56 wt % |
| (15) NaOH | 97.210 g | 97.442 g |
| Firmness | 8.10N | 4.49N |
| AP Expression | 6,001 J m-3 | 3,688 J m-3 |
| Temperature | 75.2° C. | 63.0° C. |
| Po | 1.00 | 1.00 |
| Ps | 1.00 | 1.00 |

Example 2

This example includes compositions that contain blends of crystallizing agent molecules, as determined by the BLEND TEST METHOD, contrasting the effects of the relative amounts of optimal and unsuitable chain length crystallizing agent molecules on the three required properties. Samples O-R (TABLE 5) show samples prepared using different weight percentages of typical commercial fatty acid mixtures. The header shows the particular crystallizing agent used in the preparation and the 'from analysis' shows the chain length distribution from the BLEND TEST METHOD. All the compositions failed to crystallize and could not be measured for firmness, stability temperature or aqueous phase expression. Not wishing to be bound by theory, it is believed these samples have too high a level of unsuitable crystallizing agents to initiate viable mesh formation. Samples S-V (TABLE 6) show the effect of adjusting the comparative levels of optimal and unsuitable crystallizing agent chain length in the composition. While the weight percent of the crystallizing agent remains constant in the compositions, the amount of unsuitable chain length (C10) increases, resulting in the production of softer compositions having lower thermal stability temperature that do not crystallize to form a mesh structure. Samples W-Z (TABLE 7) show the effect of adjusting the comparative levels of optimal and unsuitable crystallizing agent chain length in the composition. While the weight percent of the crystallizing agent remains constant in the compositions, the amount of unsuitable chain length (C10) increases resulting in the production of softer compositions, having lower thermal stability temperature that do not crystallize to form a mesh structure. Surprisingly, the effect of the unsuitable crystallizing agents is more detrimental in combination with the shorter chain length optimal crystallizing agent. Not wishing to be bound by theory, but it is believed that the fibrous crystals are 'held' together primarily by chain-to-chain interactions of the crystallizing agents in the crystals and, being fewer with shorter chain length crystallizing agents, are more susceptible to the presence of unsuitable crystallizing agents in the crystals.

Preparation of Compositions

Compositions were prepared using a heated mixing device. An overhead mixer (IKA Works Inc, Wilmington, N.C., model RW20 DMZ) and a three-blade impeller design was assembled. All preparations were heated on a heating-pad assembly (VWR, Radnor, Pa., 7×7 CER Hotplate, cat. no. NO97042-690) where heating was controlled with an accompanying probe. All preparations were done in a 250 ml stainless steel beaker (Thermo Fischer Scientific, Waltham, Mass.).

Samples O-R were prepared by first adding NaOH (15) and commercial fatty acid (11-14) to the beaker. The amount of NaOH was determined by acid number (AOCS Official Method Db 3-48-Free Acids or Free Alkali in Soap and Soap Products). The beaker was placed on the heating-pad assembly. The overhead stirrer was placed in the beaker and set to rotate at 100 rpm. The heater was set at 80° C. The preparation was heated to 70° C. The solution was then divided into three 60 g plastic jars (Flak-Tech, Max 60 Cup Translucent, Cat #501 222t): one jar was filled to 50 ml and two jars filled to 25 ml. They were cooled at room temperature 25 (t 3° C.). These samples remained liquid and consequently were not measured for firmness, thermal stability or water expression. One skilled in art recognizes that cooling compositions of crystallizing agent at different rates may result in modest differences in the firmness, aqueous phase expression and stability temperature properties; this is common in samples prepared at different absolute weights.

Samples S-Z were prepared by first adding Water (1) and crystallizing agent (2-7) to the beaker. The beaker was placed on the heating-pad assembly. The overhead stirrer was placed in the beaker and set to rotate at 100 rpm. The heater was set at 70° C. The preparation was heated to 70° C. The solution was then divided into three 60 g plastic jars (Flak-Tech, Max 60 Cup Translucent, Cat #501 222t): one jar was filled to 50 ml and two jars filled to 25 ml (Samples A-H). The samples were cooled at room temperature 25 (t 3° C.) until solid. Firmness measurements were made on the 50 ml sample with the FIRMNESS TEST METHOD and a thermal stability measurement was made by the THERMAL STABILITY TEST METHOD on the 50 ml sample. Aqueous phase expression measurements were made by the AQUEOUS PHASE EXPRESSION TEST METHOD on the two 25 ml samples, in all cases except Sample V and Sample Z, which remained liquid. The blend was determined from the BLEND TEST METHOD.

One skilled in art recognizes that cooling compositions of crystallizing agent at different rates may result in modest differences in the firmness, aqueous phase expression and stability temperature properties; this is common in samples prepared at different absolute weights.

TABLE 5

|  | Sample O (11)C-1270K Comparative | Sample P (12) C-1618K Comparative | Sample Q (13)C-1218K Comparative | Sample R (14) C-1214K Comparative |
| --- | --- | --- | --- | --- |
| Wt. Crystallizing Agent | 1.504 g | 1.515 g | 1.509 g | 1.511 g |
| (1) Water | 41.607 g | 43.533 g | 42.195 g | 41.708 g |
| (18) NaOH | 6.963 g | 5.020 g | 6.435 g | 6.843 g |
| % Crystallizing Agent | 3.00 wt % | 3.03 wt % | 3.00 wt % | 3.02 wt % |
| Firmness | NM1 | NM1 | NM1 | NM1 |
| AP Expression | NM5 | NM5 | NM5 | NM5 |
| Temperature | NM3 | NM3 | NM3 | NM3 |
| Po | 0.26 | 0.25 | 0.27 | 0.28 |
| Ps | [0.74] | [0.69] | [0.58] | [0.72] |
| (Chain length distribution for each crystallizing agent) | | | | |
| HC8 | — | — | — | — |
| HC10 | — | — | — | — |
| HC12 | 1.113 g | — | 0.875 g | 1.088 g |
| HC13 | — | — | — | — |
| HC14 | 0.391 g | — | 0.287 g | 0.378 g |
| HC15 | — | — | — | — |
| HC16 | — | 0.300 g | 0.121 g | 0.045 g |
| HC17 | — | — | — | — |
| HC18 | — | 0.076 g | 0.226 g | — |
| HC18:1 | — | 1.045 g | — | — |
| Other | — | 0.106 g | — | — |

TABLE 6

|  | Sample S Inventive | Sample T Inventive | Sample U Inventive | Sample V Comparative |
| --- | --- | --- | --- | --- |
| (1) Water | 47.501 g | 47.501 g | 47.500 g | 47.501 g |
| (2) NaC10 | — | 0.500 g | 1.000 g | 2.000 g |
| (3) NaC12 | — | — | — | — |
| (4) NaC14 | 2.500 g | 2.000 g | 1.505 g | 0.501 g |
| (5) NaC16 | — | — | — | — |
| (6) NaC18 | — | — | — | — |
| (7) NaC18:1 | — | — | — | — |
| % Crystallizing Agent | 5.0 wt % | 5.0 wt % | 5.1 wt % | 5.0 wt % |
| Firmness | 16.2N | 13.7N | 11.7N | NM1 |

TABLE 6-continued

|  | Sample S Inventive | Sample T Inventive | Sample U Inventive | Sample V Comparative |
|---|---|---|---|---|
| AP Expression | 8,107 J m-3 | 8,753 J m-3 | 2,176 J m-3 | NM5 |
| Temperature | 48.6° C. | 44.5° C. | 40.0° C. | NM3 |
| Po | 1.00 | 0.80 | 0.60 | 0.20 |
| Ps | 1.00 | 0.80 | 0.60 | [0.8] |

TABLE 7

|  | Sample W Inventive | Sample X Inventive | Sample Y Inventive | Sample Z Comparative |
|---|---|---|---|---|
| (1) Water | 47.502 g | 47.501 g | 47.502 g | 47.500 g |
| (2) NaC10 | — | 0.504 g | 1.500 g | 2.252 g |
| (3) NaC12 | — | — | — | — |
| (4) NaC14 | — | — | — | — |
| (5) NaC16 | — | — | — | — |
| (6) NaC18 | 2.500 g | 2.002 g | 1.003 g | 0.253 g |
| (7) NaC18:1 | — | — | — | — |
| % Crystallizing Agent | 5.0 wt % | 5.0 wt % | 5.0 wt % | 5.0 wt % |
| Firmness | 2.5N | 1.5N | 0.8N | NM1 |
| AP Expression | 4,560 J m-3 | 1,308 J m-3 | TBD | NM5 |
| Temperature | 73.0° C. | 72.6° C. | 60.6° C. | NM3 |
| Po | 1.00 | 0.80 | 0.60 | 0.10 |
| Ps | 1.00 | 0.80 | [0.60] | [0.90] |

Example 3

This include example demonstrates the effect of sodium chloride addition on the thermal stability and firmness of the personal care rheological solid composition. Samples AA-AD (TABLE 8) show the effect of adding sodium chloride into the hot mixture of crystallizing agent and aqueous phase. Sample AA is the control, without sodium chloride addition. Sample AB and Sample AC have increasing amounts of sodium chloride which results in increasing thermal stability temperature, but with a slight decrease in firmness. Surprisingly, Sample AD curds the hot mixture. Not wishing to be bound by theory, but it is believed the sodium chloride is thought to 'salt out' the crystallizing agent so that it becomes soluble only at higher temperature; and also changes the crystallization of the crystallizing agent resulting in slightly softer compositions. However, when the sodium chloride level is too high, the solubility temperature exceeds the processing temperature and the mixtures curd. Once curding has occurred, it can no longer form the crystalline mesh. Samples AE-AG demonstrate a solution to this problem. In these examples, the crystalline mesh is formed first and then the sodium chloride is physically added to the top of the personal care rheological solid composition. In this progression, the sodium chloride concentration increases the thermal stability temperature, while not changing the firmness. Not wishing to be bound by theory, it is believed that the crystalline mesh is formed as in the control Sample AA, and that the added sodium chloride diffuses through the composition to change the solubility of the fibrous crystallizing agent, but not the nature of the fibers. Curding is no longer a problem, as the mixtures are crystallized first before the salt addition. This approach provides a more than 20-degree increase in the thermal stability temperature.

Preparation of Compositions

Compositions were prepared using a heated mixing device. An overhead mixer (IKA Works Inc, Wilmington, N.C., model RW20 DMZ) and a three-blade impeller design was assembled. All preparations were heated on a heating-pad assembly (VWR, Radnor, Pa., 7×7 CER Hotplate, cat. no. NO97042-690) where heating was controlled with an accompanying probe. All preparations were done in a 250 ml stainless steel beaker (Thermo Fischer Scientific, Waltham, Mass.).

Samples AA-AD were prepared by adding Water (1), Sodium Myristate (NaM (4)) and sodium chloride (16) to the beaker. The beaker was placed on the heating-pad assembly. The overhead stirrer was placed in the beaker and set to rotate at 100 rpm. The heater was set at 80° C. The preparation was heated to 70° C. The solution was then was poured into 60 g plastic jars (Flak-Tech, Max 60 Cup Translucent, Cat #501 222t) and allowed to crystallize at 3° C. (±1° C.) in refrigerator (VWR Refrigerator, Model # SCUCFS-0204G, or equivalent) until solid. Firmness measurements were made with the FIRMNESS TEST METHOD, thermal stability measurement was made by the THERMAL STABILITY TEST METHOD and purity was determined from the BLEND TEST METHOD. Samples AE-AG were prepared by adding Water (1) and NaM (4) the beaker. The beaker was placed on the heating-pad assembly. The overhead stirrer was placed in the beaker and set to rotate at 100 rpm. The heater was set at 70° C. The preparation was heated to 70° C. The solution was then was poured into 60 g plastic jars (Flak-Tech, Max 60 Cup Translucent, Cat #501 222t) and allowed to crystallize at 3° C. (±1° C.) in refrigerator (VWR Refrigerator, Model # SCUCFS-0204G, or equivalent) until solid. The sodium chloride (16) was added to the top of the composition and allowed to diffuse through the composition for one week, before measurement. Firmness measurements were made with the FIRMNESS TEST METHOD, thermal stability measurement was made by the THERMAL STABILITY TEST METHOD and purity was determined from the BLEND TEST METHOD. One skilled in art recognizes that cooling compositions of crystallizing agent at different rates may result in modest differences in the firmness, aqueous phase expression and stability temperature properties; this is common in samples prepared at different absolute weights.

TABLE 8

|  | Sample AA Inventive | Sample AB Inventive | Sample AC Inventive | Sample AD Comparative |
|---|---|---|---|---|
| (1) Water | 48.531 g | 48.070 g | 47.028 g | 43.742 g |
| (4) NaM | 1.519 g | 1.512 g | 1.478 g | 1.358 g |
| % Crystallizing Agent | 3.03 wt % | 3.02 wt % | 2.95 wt % | 2.70 wt % |
| (16) NaCl | — | 0.508 g | 1.524 g | 5.087 g |
| Wt % NaCl | — | 1.0 wt % | 3.0 wt % | 10.1 wt % |
| Firmness | 6.51N | 3.77N | 3.15N | NM2 |
| Stability Temp | 54.0° C. | 61.6° C. | 64.7° C. | NM4 |
| Po | 1.00 | 1.00 | 1.00 | 1.00 |
| Ps | 1.00 | 1.00 | 1.00 | 1.00 |

TABLE 9

|  | Sample AE Inventive | Sample AF Inventive | Sample AG Inventive |
|---|---|---|---|
| Water | 48.0 g | 47 g | 43.6 g |
| NaM | 1.5 g | 1.5 g | 1.35 g |
| % Crystallizing Agent | 3.00 wt % | 3.00 wt % | 2.70 wt % |
| NaCl (post) | 0.5 g | 1.5 g | 5.0 g |
| Wt % NaCl | 1.0 wt % | 3.0 wt % | 10.1 wt % |
| Firmness | 8.47N | 9.31N | 9.53N |
| Stability Temp | 55.5° C. | 61.7° C. | 76.7° C. |
| Po | 1.00 | 1.00 | 1.00 |
| Ps | 1.00 | 1.00 | 1.00 |

Example 4

This example illustrates the difference between inventive samples in this specification relative to bar soap compositions, exemplified by Sample AH. The example fails to meet all three performance criteria. Specifically, the thermal stability temperature of the composition is too low to effectively survive reliably on the shelf life or in the supply chain. Not wishing to be bound by theory, it is believed the chain length of 12 is far too soluble owing to the short chain length (i.e. Sample J) such that—even with a 1 wt % addition of the sodium chloride, the C12 solubilizes below 40° C.

Preparation of Compositions

Compositions were prepared using a heated mixing device. An overhead mixer (IKA Works Inc, Wilmington, N.C., model RW20 DMZ) and a three-blade impeller design was assembled. All preparations were heated on a heating-pad assembly (VWR, Radnor, Pa., 7×7 CER Hotplate, cat. no. NO97042-690) where heating was controlled with an accompanying probe. All preparations were done in a 250 ml stainless steel beaker (Thermo Fischer Scientific, Waltham, Mass.).

A solution was prepared by adding water (1), sodium chloride (16) and lauric acid (17) to the beaker. The beaker was placed on the heated mixing device. The overhead stirrer was placed in the beaker and set to rotate at 100 rpm. The heater was set and the preparation was heated to 71° C. Sodium hydroxide (15) was then added to the solution to neutralize the fatty acid and the entire mixture was heated to 95° C. The solution was then placed in cooling jars (Flak-Tech, Max 60 Cup Translucent, Cat #501 222t) and set on the bench to cool at room temperature 25 (t 3° C.) until solid. Firmness measurements were made with the FIRMNESS TEST METHOD, thermal stability measurement was made by the THERMAL STABILITY TEST METHOD, water expression was made by the AQUEOUS PHASE EXPRESSION TEST METHOD and purity was determined from the BLEND TEST METHOD.

TABLE 10

|  | Sample AH Comparative |
|---|---|
| (1) Water | 71.500 g |
| (16) NaCl | 1.002 g |
| (17) HL | 4.506 g (22.5 mmol) |
| (15) NaOH | 22.500 g (563 mmol) |
| % Crystallizing Agent | 5.0 wt % |
| Firmness | 11.43N |
| AP Expression | 2,810 J m-3 |
| Stability Temp. | 35.5° C. |
| Po | 0.00 |
| Ps | [1.00] |

Example 5

Response of the Compositions to Shear Stress During Use; As shown in FIG. 3

As measured by amount of composition dispensed from a stick composition prepared from 3 wt % crystallizing agent in water, with practical process conditions.

Compositions were prepared using a heated mixing device. An overhead mixer (IKA Works Inc, Wilmington, N.C., model RW20 DMZ) and a three-blade impeller design was assembled. All preparations were heated on a heating-pad assembly (VWR, Radnor, Pa., 7×7 CER Hotplate, cat. no. NO97042-690) where heating was controlled with an accompanying probe. All preparations were done in a 125 ml stainless steel beaker (Thermo Fischer Scientific, Waltham, Mass.).

Solutions were prepared by adding water 97% water and 3% crystallizing agent (with specific chain length) to the beaker. The beaker was placed on the heated mixing device. The overhead stirrer was placed in the beaker and set to rotate at 225 rpm. The heater was set, and the preparation was heated to precisely 70° C. The solution was then poured in a face stick container (Qosmedix, Ronkonkoma, N.Y., Round Twist-Up Deodorant Container and Cap, Black, cat. no. 30006; Albea, France, Skyline Face Stick) and allowed to cool overnight at room temperature.

The plastic 'lid' was removed from the stick, and the stick was weighed. The stick was gently swiped across a human panelist's arm five times, then weighed again. This was repeated with at least three different panelists, and the differences averaged. The reported value in FIG. 3 is the average weight loss in grams of all three trials. A smaller value means less residue on the skin. Note: there is a discontinuous jump in the residue at C18. Not wishing to be bound by theory, it is thought that C18 (and longer chain length crystallizing agents) have both insufficient hydrophilic-hydrophobic balance and are too close (or above) practical process temperature, to form effective crystals and a crystalline mesh of fiber-like crystalline particles.

Example 6

Materials
(1) Water
(4) Sodium myristate (NaC14)
(19) Ethanol: EMD Millipore Corporation, Cat # EX0276-4
(20) L-Menthol
(21) Frescolat MGA
(16) Sodium chloride (NaCl)

This example demonstrates a composition for a skin cooling composition, that contains a combination of ethanol and two sensates, MGA and menthol. The ethanol adds an 'immediate', enhanced cooling sensation resulting from the evaporation of ethanol in combination with water; the combination of sensate adds a 'long lasting' cooling sensation. The entirety of samples speaks to the complexities of formulation design. It is noted that in the absence of ethanol and sensate, the chain length of 14 make very firm and thermally stable personal care rheological solid compositions. However, the inclusion of both ethanol and sensate into the composition softens the composition and lowers the thermal stability temperature (Sample AI-AL), relative to non-ethanol and non-sensate compositions. In fact, Samples AI and Sample AJ no longer meet all three performance criteria. The samples in this example were placed in an oven at 40° C., where samples that turned to liquid were considered comparative examples. Sample AL is too firm to express water for good cooling. Lowering the level of the sensate (Sample AM) increases the thermal stability temperature but also reduces the long lasting cooling sensation; raising the level of the sensate (Sample AN) makes achieving needed thermal stability a challenge. Addition of modest amounts of sodium chloride (Sample AO and Sample AP) allows higher levels of sensate in compositions that remain thermally stable.

Preparation of Compositions

Compositions were prepared using a heated mixing device. An overhead mixer (IKA Works Inc, Wilmington, N.C., model RW20 DMZ) and a three-blade impeller design was assembled. All preparations were heated on a heating-pad assembly (VWR, Radnor, Pa., 7×7 CER Hotplate, cat. no. NO97042-690) where heating was controlled with an accompanying probe.

The solutions were prepared by adding water (1) and sodium myristate (4) a stainless steel beaker (Thermo Fischer Scientific, Waltham, Mass.). The beaker is placed on the heated mixing device. The overhead stirrer was placed in the beaker and set to rotate at 100 rpm. The heater was set to 80° C. The preparation was heated to 70° C. The solution was then cooled down to 60° C. at which time the menthol (20), ethanol (19) and MGA (21) were added and mixed until thoroughly dissolved. Sodium chloride (16) was added and further mixed until thoroughly dissolved. The solution was then divided into three 60 g plastic jars (Flak-Tech, Max 60 Cup Translucent, Cat #501 222t): one jar was filled to 50 ml and two jars filled to 25 ml (Samples A-H). The samples were cooled at room temperature 25° C. (t 3° C.) until solid. Firmness measurements were made on the 50 ml sample with the FIRMNESS TEST METHOD and a thermal stability measurement was made by the THERMAL STABILITY TEST METHOD on the 50 ml sample. Water-expression measurements were made by the WATER-EXPRESSION TEST METHOD on the two 25 ml samples. A value of 'NM' in TABLE 11 and TABLE 12, means that a composition was pre-screened by placing the composition in an over set at 40° C. for 60 minutes, and was not tested further if the resulting sample was completely or partially liquid.

TABLE 11

|  | Sample AI Comparative | Sample AJ Comparative | Sample AK Comparative | Sample AL Inventive |
|---|---|---|---|---|
| (1) Water | 90.641 g | 88.640 g | 86.642 g | 84.627 g |
| (4) NaC14 | 4.001 g | 6.001 g | 8.004 g | 10.001 g |
| (19) Ethanol | 4.003 g | 4.004 g | 4.000 g | 4.000 g |
| (20) L-Menthol | 0.230 g | 0.232 g | 0.234 g | 0.232 g |
| (21) MGA | 1.140 g | 1.141 g | 1.144 g | 1.140 g |
| (16) NaCl | — | — | — | — |
| % Crystallizing Agent | 4.0 wt % | 6.0 wt % | 8.0 wt % | 9.8 wt % |
| Firmness | 1.8N | 10.0N | 24.8N | 31.5N |
| Water Expression | NM | NM | 525.6 J m-3 | 3,388.7 J m-3 |
| Temperature | NM | NM | 36.6° C. | 40.0° C. |
| Purity - Po | 1.0 | 1.0 | 1.0 | 1.0 |
| Purity - Ps | 1.0 | 1.0 | 1.0 | 1.0 |

TABLE 12

|  | Sample AM Comparative | Sample AN Comparative | Sample AO Inventive | Sample AP Inventive |
|---|---|---|---|---|
| (1) Water | 89.541 g | 89.091 g | 88.090 g | 82.642 g |
| (4) NaC14 | 6.001 g | 6.000 g | 6.000 g | 6.003 g |

TABLE 12-continued

|  | Sample AM Comparative | Sample AN Comparative | Sample AO Inventive | Sample AP Inventive |
|---|---|---|---|---|
| (19) Ethanol | 4.000 g | 4.000 g | 4.003 g | 4.004 g |
| (20) L-Menthol | 0.083 g | 0.153 g | 0.151 g | 0.232 g |
| (21) MGA | 0.381 g | 0.761 g | 0.761 g | 1.140 g |
| (16) NaCl | — | — | 1.002 g | 6.002 g |
| % Crystallizing Agent | 6.0 wt % | 6.0 wt % | 6.0 wt % | 6.0 wt % |
| Firmness | 21.2N | 16.1N | 13.7N | 12.9N |
| Water Expression | 4,666.9 J m-3 | NM | 1,520 J m-3 | — |
| Temperature | 36.4° C. | NM | 43.9° C. | 58.2° C. |
| Purity - Po | 1.0 | 1.0 | 1.0 | 1.0 |
| Purity - Ps | 1.0 | 1.0 | 1.0 | 1.0 |

Example 7

Materials
(1) Water
(4) Sodium myristate (NaC14)
(22) Glycerin: Alfa Aesar, Cat # A16205

This example demonstrates creating stick compositions that provide a moisturization benefit when applied to skin.

Preparation of Compositions

Compositions were prepared using a heated mixing device. An overhead mixer (IKA Works Inc, Wilmington, N.C., model RW20 DMZ) and a three-blade impeller design was assembled. All preparations were heated on a heating-pad assembly (VWR, Radnor, Pa., 7×7 CER Hotplate, cat. no. NO97042-690) where heating was controlled with an accompanying probe.

The solutions were prepared by adding water (1) and sodium myristate (4) a stainless steel beaker (Thermo Fischer Scientific, Waltham, Mass.). The beaker is placed on the heated mixing device. The overhead stirrer was placed in the beaker and into the mixture, and set to rotate at 100 rpm. The mixture was heated to 70° C. The solution was then cooled down to 60° C. at which time the glycerin (22) was added and mixed thoroughly for about five minutes. The solution was then added to a 60-gram speed-mixer cup (Flak-Tech, Max 60 Cup Translucent, Cat #501 222t) and set quiescently to cool at room temperature 25° C. (t 3° C.). Firmness measurements were made on the 50 ml sample with the FIRMNESS TEST METHOD and a thermal stability measurement was made by the THERMAL STABILITY TEST METHOD on the 50 ml sample. Water-expression measurements were made by the WATER-EXPRESSION TEST METHOD on the two 25 ml samples.

TABLE 13

|  | Sample AQ Inventive | Sample AR Inventive | Sample AS Inventive | Sample AT Inventive |
|---|---|---|---|---|
| (1) Water | 49.001 g | 46.501 g | 44.001 g | 43.001 g |
| (4) NaC14 | 1.001 g | 1.001 g | 1.000 g | 2.001 g |
| (22) Glycerin | — | 2.501 g | 5.003 g | 5.000 g |
| % Crystallizing Agent | 2.0 wt % | 2.0 wt % | 2.0 wt % | 4.0 wt % |
| Firmness | 4.0N | 5.1N | 5.6N | 12.5N |
| Water Expression | 2,370 J m-3 | 2,810 J m-3 | 3,250 J m-3 | 9,210 J m-3 |
| Temperature | 46.8° C. | 46.4° C. | 45.3° C. | 51.0° C. |
| Purity - Po | 1.0 | 1.0 | 1.0 | 1.0 |
| Purity - Ps | 1.0 | 1.0 | 1.0 | 1.0 |

Sample AQ is a control without glycerin. Samples AR-AT show that adding small amounts of glycerin, about 2-4 wt %, provide compositions with glycerin that maintain their ability to express water. Samples AU-AV show that adding larger amounts of glycerin, about 6-9 wt %, provide compositions with glycerin that no longer effectively express water. Samples AU-AV also starkly illustrate why high-glycerin (or high polyol) compositions, as reflected in the previously disclosed art, do not express water.

TABLE 14

|  | Sample AU Comparative | Sample AV Comparative |
|---|---|---|
| (1) Water | 42.001 g | 81.003 g |
| (4) NaC14 | 3.001 g | 9.004 g |
| (22) Glycerin | 5.003 g | 10.004 g |
| % Crystallizing Agent | 6.0 wt % | 9.0 wt % |
| Firmness | 28.0N | 45.3N |
| Water Expression | NM | NM |
| Temperature | 47.5° C. | 52.4° C. |
| Purity - Po | 1.0 | 1.0 |
| Purity - Ps | 1.0 | 1.0 |

Example 8

Materials
(1) Water
(23) Xanthan Gum (X-gum)—CPK, Denmark, Keltrol 1000, LOT 6J3749K
(24) Konjac Gum (K-gum)—FMC Corporation, Philadelphia, Pa., Nutricol® XP 3464, FMC, LOT 1192605.
(25) Euxyl PE 9010—Schülke & Mayr GmbH, Norderstedt, Germany, PE 9010 preservative lot 1501226.
(26) SymDiol 68—Symrise, Holzminden, Germany, Symdiol® 68 preservative lot 10300094).

(4) Sodium Myristate (NaC14)
(5) Sodium Palmitate (NaC16)
(6) Sodium Stearate (NaC18)
(27) Mosa Mint Oil
(16) Sodium chloride (NaCl)

The compositions of the EXAMPLE contain crystallizing agents that form a mesh to enable the composition to be solid. Water is dispersed throughout the mesh to create an aqueous composition.

The essential oils are also dispersed and immobilized throughout the mesh. However, essential oils and water are incompatible materials. The invention uses two elements to enable the formation of the personal care rheological solid composition. First, a suspension agent is used to prevent separation of the oil and water during making. Second, sodium chloride is used to speed up the crystallization of the crystallizing agent. These are balanced correctly to achieve a homogenous solid, rather than a soft or liquid composition.

The basic elements of the personal care rheological solid composition include crystallizing agent, essential oil, suspension agent, preservative and sodium chloride, blended in the right proportions to achieve a solid composition. The suspension agent is a blend or x-gum and k-gum, which interact in the mixture to create a small yield stress that keeps the essential oil suspended until complete crystallization of the crystallizing agent. A properly suspended mixture has evenly dispersed essential oil droplets in the final composition. A preservative is added to protect the gums against microbial growth. TABLE 15 demonstrates that there may be an upper concentration of essential oil in the personal care rheological solid composition. Samples AW and AX have 1 wt % to 3 wt % essential oil respectively and are solid compositions. Samples AY and AZ have 5 wt % to 7 wt % essential oil, respectively, and are no longer solid compositions. TABLE 16 demonstrates that the composition requires a minimal amount of suspension agent. Sample BA has only 0.05 wt % suspension agent, and the oil separates from the mixture. Samples BB and BC have 0.10 wt % and 0.20 wt % respectively, of suspension agent and the oil remains dispersed as droplets in the mixtures. TABLE 17 demonstrates the utility of added salt to create good compositions. Sample BD is a control with no essential oil. Sample BE has 3 wt % essential oil but is unstable in the absence of sodium chloride. Sample BF and BG with higher levels of sodium chloride added result in stable compositions. TABLE 18 demonstrates that the compositions can be achieved with different chain lengths of crystallizing agent. Samples BH and BI are prepared with sodium myristate, sodium palmitate and sodium stearate, respectively. Finally, TABLE 19 shows that the crystallization temperature can aid in the formation of the composition. Sample BK is cooled at room temperature which is not fast enough to prevent separation of the essential oils during processing. However, sample BL cools the composition more rapidly resulting in a solid composition. Not wishing to be bound by theory, it is believed that better crystallization occurs if crystallization occurs faster. The lower crystallization temperature speeds the crystallization process.

Preparation of Compositions (A1) Preparation of 1 wt % Xanthan Gum Stock (X-Gum Stock)

0.202 grams Euxyl PE 9010 (25), 0.305 grams SymDiol 68 (26) and 49.007 grams of water (1) were added to a Max 60 Speed Mixer cup (Flak-Tech, Max 60 Cup Translucent, Cat #501 222t). 0.502 grams xanthan gum (23) were added to the cup. The cup was placed in the Speed Mixer (Flak-Tech) at 2700 rpm for 150 seconds. Samples were allowed to sit for 2 hours and then Speed Mixed a second time for 2700 rpm for 150 seconds.

(A2) Preparation of 1 wt % Konjac Gum Stock (K-Gum Stock)

0.201 grams Euxyl PE 9010 (25), 0.301 grams SymDiol 68 (26) and 49.001 grams of water (1) were added to a Max 60 Speed Mixer cup (Flak-Tech, Max 60 Cup Translucent, Cat #501 222t). 0.503 grams konjac gum (24) were added to the cup. The cup was placed in the Speed Mixer at 2700 rpm for 150 seconds. Samples were allowed to sit for 2 hours and then Speed Mixed a second time for 2700 rpm for 150 seconds.

Preparation of Compositions

Compositions were prepared using a heated mixing device. An overhead mixer (IKA Works Inc, Wilmington, N.C., model RW20 DMZ) and a three-blade impeller design was assembled. All preparations were heated on a heating-pad assembly (VWR, Radnor, Pa., 7×7 CER Hotplate, cat. no. N097042-690) where heating was controlled with an accompanying probe.

The solutions were prepared by adding water (1), sodium myristate (4), Euxyl PE 9010 (25), and Symdiol 68(26) to a stainless steel beaker (Thermo Fischer Scientific, Waltham, Mass.). The beaker was placed on the heated mixing device. The overhead stirrer was placed in the beaker and into the mixture and set to rotate at 100 rpm. The mixture was heated to 70° C. until the crystallizing agent was completely dissolved and the mixture transparent. The solution was then cooled to 60° C. at which point X-gum Stock (A1) and K-gum Stock (A2) were added along with Mosa Mint oil (27). The solution was allowed to mix until emulsion drops were dispersed before the NaCl was added. The final preparations were placed in cooling jars (Flak-Tech, Max 60 Cup Translucent, Cat #501 222t) on the bench at room temperature 25° C. (t 3° C.) or in a refrigerator at 4° C. (t 1° C.) (VWR Refrigerator, Model # SCUCFS-0204G, or equivalent). The final composition was assessed as whether it formed a rheological solid.

TABLE 15

|  | Sample AW Inventive | Sample AX Inventive | Sample AY Comparative | Sample AZ Comparative |
| --- | --- | --- | --- | --- |
| (1) Water | 34.000 g | 33.001 g | 34.500 g | 29.501 g |
| (25) Euxyl PE 9010 | 0.200 g | 0.400 g | 0.200 g | 0.204 g |
| (26) Symdiol 68 | 0.300 g | 0.602 g | 0.303 g | 0.301 g |
| (4) NaC14 | 2.501 g | 2.501 g | 2.501 g | 2.501 g |
| (5) NaC16 | — | — | — | — |
| (6) NaC18 | — | — | — | — |
| (A1) X-gum premix | 4.003 g | 4.003 g | 4.001 g | 4.003 g |
| (A2) K-gum premix | 6.000 g | 6.000 g | 6.003 g | 6.003 g |
| (27) Mint Oil | 0.504 g | 1.501 g | 2.500 g | 5.000 g |

TABLE 15-continued

|  | Sample AW Inventive | Sample AX Inventive | Sample AY Comparative | Sample AZ Comparative |
|---|---|---|---|---|
| % Oil | 1.0 wt % | 3.0 wt % | 5.0 wt % | 10.0 wt % |
| (16) NaCl | 2.502 g | 2.502 g | 2.500 g | 2.502 g |
| Cooling Temp | 25° C. | 25° C. | 25° C. | 25° C. |

TABLE 16

|  | Sample BA Comparative | Sample BB Inventive | Sample BC Inventive |
|---|---|---|---|
| (1) Water | 40.502 g | 38.000 g | 33.001 g |
| (25) Euxyl PE 9010 | 0.204 g | 0.200 g | 0.200 g |
| (26) Symdiol 68 | 0.304 g | 0.303 g | 0.302 g |
| (4) NaC14 | 2.501 g | 2.502 g | 2.501 g |
| (5) NaC16 | — | — | — |
| (6) NaC18 | — | — | — |
| (A1) X-gum premix | 1.002 g | 2.004 g | 4.003 g |
| (A2) K-gum premix | 1.500 g | 3.004 g | 6.000 g |
| % Aid | 0.05 wt % | 0.10 wt % | 0.20 wt % |
| (27) Mint Oil | 1.502 g | 1.504 g | 1.501 g |
| (16) NaCl | 2.500 g | 2.502 g | 2.502 g |
| Cooling Temp | 25° C. | 25° C. | 25° C. |

TABLE 17

|  | Sample BD Inventive | Sample BE Comparative | Sample BF Inventive | Sample BG Inventive |
|---|---|---|---|---|
| (1) Water | 36.501 | 35.000 g | 34.500 g | 33.001 g |
| (25) Euxyl PE 9010 | 0.400 | 0.400 g | 0.400 g | 0.400 g |
| (26) Symdiol 68 | 0.601 | 0.601 g | 0.600 g | 0.602 g |
| (4) NaC14 | 2.502 | 2.503 g | 2.500 g | 2.501 g |
| (5) NaC16 | — | — | — | — |
| (6) NaC18 | — | — | — | — |
| (A1) X-gum premix | 4.001 | 4.003 g | 4.000 g | 4.003 g |
| (A2) K-gum premix | 6.001 | 6.002 g | 6.000 g | 6.000 g |
| (27) Mint Oil | — | 1.503 g | 1.500 g | 1.501 g |
| (16) NaCl | — | — | 0.500 g | 2.502 g |
| % NaCl | 0 wt % | 0 wt % | 1 wt % | 5 wt % |
| Cooling Temp | 25° C. | 25° C. | 25° C. | 25° C. |

TABLE 18

|  | Sample BH Inventive | Sample BI Inventive |
|---|---|---|
| (1) Water | 33.002 g | 33.001 g |
| (25) Euxyl PE 9010 | 0.200 g | 0.203 g |
| (26) Symdiol 68 | 0.304 g | 0.303 g |
| (4) NaC14 | 2.501 g | — |
| (5) NaC16 | — | 2.504 g |
| (6) NaC18 | — | — |
| (A1) X-gum premix | 4.001 g | 4.002 g |
| (A2) K-gum premix | 6.001 g | 6.000 g |
| (27) Mint Oil | 1.503 g | 1.503 g |
| (16) NaCl | 2.502 g | 2.500 g |
| Cooling Temp | 4° C. | 4° C. |

TABLE 19

|  | Sample BK Comparative | Sample BL Inventive |
|---|---|---|
| (1) Water | 38.000 g | 38.000 g |
| (25) Euxyl PE 9010 | 0.200 g | 0.202 g |
| (26) Symdiol 68 | 0.303 g | 0.301 g |
| (4) NaC14 | 2.502 g | 2.502 g |
| (5) NaC16 | — | — |
| (6) NaC18 | — | — |
| (A1) X-gum premix | 2.004 g | 2.000 g |
| (A2) K-gum premix | 3.004 g | 3.000 g |
| (27) Mint Oil | 1.504 g | 1.502 g |
| (16) NaCl | 2.502 g | 2.501 g |
| Cooling Temp | 25° C. | 4° C. |

Example 8

Materials
(1) Water
(4) Sodium myristate (NaC14)
(5) Sodium palmitate (NaC16)
(6) Sodium stearate (NaC18)
(28) Triclosan (TCS)
(29) Triclocarban (TCC)
(30) Perfumes Sample BM-BP are inventive deodorant compositions. BM is a modest firmness, low residue composition containing a minimum amount of an antimicrobial to control odor. It also contains two perfumes: 1) odor perfume (perfume 1) to mask any odor and 2) character perfume (perfume 2) to provide contextual branding. BN is a slightly firmer, moderate residue composition containing two antimicrobial actives to more effectively control odor. It also contains two perfumes: 1) odor perfume (perfume 1) to mask any odor and 2) character perfume (perfume 2) to provide contextual branding. BN is a slightly firmer, moderate residue composition containing two antimicrobial actives at the highest concentration for the most effectively control odor. It also contains two perfumes at the highest levels: 1) odor perfume (perfume 1) to mask any odor and 2) character perfume (perfume 2) to provide contextual branding. BP is a firm, low residue composition containing only one single antimicrobial active at the highest concentration for effective control odor. It also contains two perfumes at the highest levels: 1) odor perfume (perfume 1) to mask any odor and 2) character perfume (perfume 2) to provide contextual branding. As with TABLE 15-19, these compositions may require secondary suspension agents such as with the x-gum and k-gum as previously described, to keep large amounts of perfume oils suspended as droplets during the crystallization of the crystallizing agent. The composition may also require sodium chloride up to 5-8 wt % to raise the thermal transition temperature. Optionally, these compositions include up to 5 wt % glycerin.

Preparation of Compositions

Compositions are prepared using a heated mixing device. An overhead mixer (IKA Works Inc, Wilmington, N.C., model RW20 DMZ) and a three-blade impeller design is assembled. All preparations are heated on a heating-pad assembly (VWR, Radnor, Pa., 7×7 CER Hotplate, cat. no. NO97042-690) where heating is controlled with an accompanying probe.

The solutions were prepared by adding water (1) and crystallizing agent (4, 5, 6 or combinations) to a stainless-steel beaker (Thermo Fischer Scientific, Waltham, Mass.). The beaker was placed on the heated mixing device. The overhead stirrer was placed in the beaker and into the mixture and set to rotate at 100 rpm. The mixture was heated to 90° C. until the crystallizing agent was completely dissolved and the mixture transparent. The solution was then cooled to 40° C. at which point the antimicrobial (28, 29) and optionally perfume(s) (30) were added to the mixture. The actives were added as quick as possible, before significant crystallization occurs in the mixture. The final mixture was placed in cooling jars (Flak-Tech, Max 60 Cup Translucent, Cat #501 222t) on the bench at room temperature 25° C. (t 3° C.) or in a refrigerator at 4° C. (t 1° C.) (VWR Refrigerator, Model # SCUCFS-0204G, or equivalent).

TABLE 20

|  | Sample BM Inventive | Sample BN Inventive | Sample BO Inventive | Sample BP Inventive |
| --- | --- | --- | --- | --- |
| (1) Water | 95.9 g | 93.8 g | 91.9 g | 93.2 g |
| (4) NaC14 | 2.0 g | — | — | 4.0 g |
| (5) NaC16 | — | 4.0 g | — | — |
| (6) NaC18 | — | — | 5.0 g | — |
| (28) TCS | — | 0.1 g | 0.3 g | — |
| (29) TCC | 0.1 g | 0.1 g | 0.3 g | 0.3 g |
| (30) Perfume 1 | 1.0 g | 1.0 g | 1.7 g | 1.7 g |
| (30) Perfume 2 | 1.0 g | 1.0 g | 1.8 g | 1.8 g |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care rheological solid composition comprising:
    a crystallizing agent; an aqueous phase comprising at least about 80 wt % water; and NaCl;
    wherein, the personal care rheological solid composition has a firmness between about 1.0 N to about 20.0 N as determined by the FIRMNESS TEST METHOD using a texture analyzer at room temperature;
    a thermal stability of about 40° C. to about 95° C. as determined by the THERMAL STABILITY TEST METHOD using a differential scanning calorimeter (DSC);
    a liquid expression of between about 100 J m-3 to about 8,000 J m-3 as determined by the AQUEOUS PHASE EXPRESSION TEST METHOD using a rheometer at room temperature; and
    wherein the crystallizing agent is a blend of sodium salts of fatty acids containing from 13 to 20 carbon atoms; wherein the crystallizing agent blend has an Optimal Purity (Po) of greater than about 0.3 and a Single Purity (Ps) of greater than about 0.5 as determined by the BLEND TEST METHOD;
    wherein the amount of crystallizing agent in the composition is between about 0.5% and about 7% by weight of the rheological solid composition.

2. The personal care rheological solid composition of claim 1, wherein the personal care rheological solid composition comprises a NaCl concentration of at most 10 wt %.

3. The personal care rheological solid composition of claim 1 wherein the sodium salts are at least two of sodium stearate, sodium palmitate, sodium myristate, sodium tridecanoate, sodium pentadecanoate, sodium heptadecanoate and sodium nonadecanoate.

4. The personal care rheological solid composition of claim 1, wherein, the personal care rheological solid composition has the firmness between about 5.0 N to about 10.0 N as determined by the FIRMNESS TEST METHOD using the texture analyzer at room temperature.

5. The personal care rheological solid composition of claim 1, wherein the personal care rheological solid composition has the thermal stability from about 45° C. to about 80° C. as determined by the THERMAL STABILITY TEST METHOD using the DSC.

6. The personal care rheological solid composition of claim 1, wherein the personal care rheological solid composition has a liquid expression of between about 1,000 J m-3 to about 7,000 J m-3 as determined by the AQUEOUS PHASE EXPRESSION TEST METHOD using the rheometer at room temperature.

7. The personal care rheological solid composition of claim 1, wherein the personal care rheological solid composition has a liquid expression of between about 2,000 J m-3 to about 5,000 J m-3 as determined by the AQUEOUS PHASE EXPRESSION TEST METHOD using the rheometer at room temperature.

\* \* \* \* \*